US010093945B2

(12) United States Patent
Gundersen-Rindal et al.

(10) Patent No.: US 10,093,945 B2
(45) Date of Patent: Oct. 9, 2018

(54) **DOUBLE STRAND RNA-MEDIATED RNA INTERFERENCE THROUGH FEEDING DETRIMENTAL TO LARVAL *LYMANTRIA DISPAR* (GYPSY MOTH)**

(71) Applicant: The United States of America, as Represented by the Secretary of Agriculture, Washington, DC (US)

(72) Inventors: Dawn E. Gundersen-Rindal, Silver Spring, MD (US); Saikat Kumar B. Ghosh, Columbia, MD (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 178 days.

(21) Appl. No.: 14/940,861

(22) Filed: Nov. 13, 2015

(65) Prior Publication Data

US 2017/0137841 A1    May 18, 2017

(51) Int. Cl.
| | | |
|---|---|---|
| *C12N 15/82* | (2006.01) | |
| *C12N 15/113* | (2010.01) | |
| *A01N 57/16* | (2006.01) | |
| *A01N 63/00* | (2006.01) | |
| *A01N 37/46* | (2006.01) | |
| *A01N 63/02* | (2006.01) | |

(52) U.S. Cl.
CPC ......... *C12N 15/8286* (2013.01); *A01N 37/46* (2013.01); *A01N 57/16* (2013.01); *A01N 63/00* (2013.01); *A01N 63/02* (2013.01); *C12N 15/113* (2013.01); *C12N 15/1137* (2013.01); *C12N 2310/14* (2013.01)

(58) Field of Classification Search
CPC .................................................. C12N 15/8286
USPC ........................................................ 800/279
See application file for complete search history.

(56) References Cited

U.S. PATENT DOCUMENTS 6,326,193 B1  12/2001  Liu et al.
8,415,320 B2   4/2013  Whyard et al.

FOREIGN PATENT DOCUMENTS

EP    1971688 B1    3/2012

OTHER PUBLICATIONS

Thomas et al. 2001, The Plant Journal 25(4):417-425.*
Huvenne, Hanneke et al., "Review: Mechanism of dsRNA Uptake in Insects and Potential of RNAi for Pest Control: A Review," (2010) Journal of Insect Physiology, 56:227-235.
Linquist, Alicia G., "Knockdown of Vitellogenin by RNAi Increases Survivorship But Exhibits Similar Physiological Responses to Ovariectomy in Grasshoppers," UNF Digital Commons, (2013) UNF Theses and Dissertations. Paper 477.
Gordon, Karl H. J. et al., "RNAi for Insect-Proof Plants," (2007) Nature Biotechnology vol. 25:(11).
Christiaens, O. et al., "The Challenge of RNAi-mediated Control of Hemipterans," (2014) Science Direct Current Opinion in Insect Science 6:15-21.
Huvenne, Hanneke et al., "Review: Mechanism of dsRNA Uptake in Insects and Potential of RNAi for Pest Control: A Review," (2009) Journal of Insect Physiology, 56:227-235.
Zhang, Hao et al., "Feasibility, Limitation and Possible Solutions of RNAi-based Technology for Insect Pest Control," (2013), Insect Science, 20:15-30, DOI 10.1111/j.-1744-7917.2012.01513.x.
Burand, John P. et al., "RNAi: Future in Insect Management," (2013) Journal of Invertebrate Pathology, 112:S68-S74.

* cited by examiner

*Primary Examiner* — Li Zheng
(74) *Attorney, Agent, or Firm* — John D. Fado; Mark D. McNemar

(57) ABSTRACT

The present invention relates to the field of double-stranded RNA (dsRNA)-mediated gene silencing in insect species. More particularly, the present invention relates to genetic constructs designed for the expression of dsRNA corresponding to novel target genes in the insect pest *Lymantria dispar*, commonly known as the gypsy moth. The present invention also provides methodologies for introducing dsRNA into target insects to induce RNA interference. These constructs are particularly useful in RNAi-mediated control of the gypsy moth.

21 Claims, 7 Drawing Sheets
Specification includes a Sequence Listing.

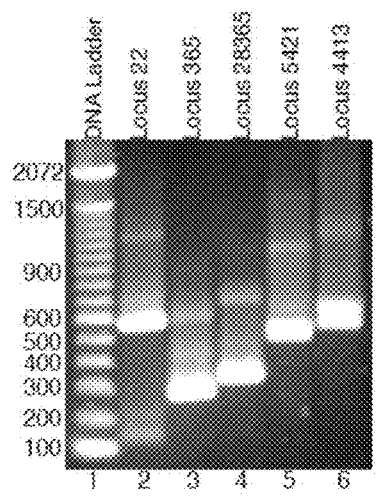 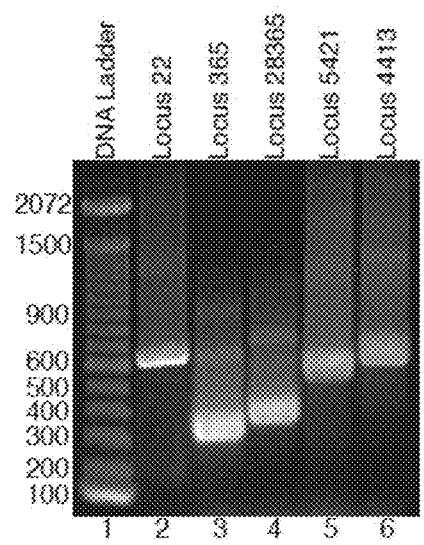
FIG. 3A  FIG. 3B
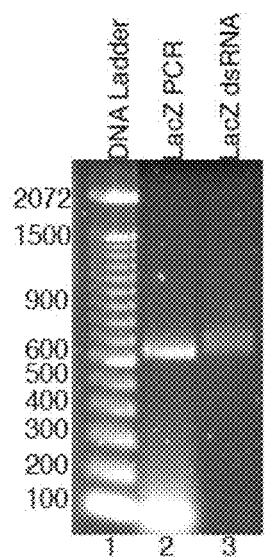
FIG. 3C

DOUBLE STRAND RNA-MEDIATED RNA INTERFERENCE THROUGH FEEDING DETRIMENTAL TO LARVAL *LYMANTRIA DISPAR* (GYPSY MOTH)

BACKGROUND OF THE INVENTION

Field of Invention

The present invention relates to the field of double-stranded RNA (dsRNA)-mediated gene silencing in insect species. More particularly, the present invention relates to genetic constructs designed for the expression of dsRNA corresponding to novel target genes in the insect pest *Lymantria dispar*, commonly known as the gypsy moth. These constructs are particularly useful in RNAi-mediated control of the gypsy moth.

Background

*Lymantria dispar* (Lepidoptera: Erebidae), the gypsy moth, is the most serious insect pest of the North American forests where larvae feed on over 300 tree and shrub species, especially hardwood and shade trees. Measures to control the pest and reduce its spread have been implemented in the United States, including augmentative release of natural enemies, use of chemical pesticides (acephate=Orthene®, carbaryl=Sevin®, and diflubenzuron=Dimilin®), mating disruption using a chemical pheromone (Disparlure), and use of microbial biopesticides such as the nucleopolyhedrovirus (Gypchek®) or the gram-positive soil bacterium *Bacillus thuringiensis* (Bt) (Höfte & Whiteley, Microbiol. Revs., (1989) 53:2, 242-55). These measures have been employed with variable success and resistance to biopesticides has evolved rapidly in larval populations. Recently publicly available data sets for gypsy moth-associated genes were generated through characterization of transcriptomes of both an *L. dispar*-derived cell line IPLB-Ld652Y (Sparks & Gundersen-Rindal, Viruses, (2011) 3:12, 2339-50) and the *L. dispar* larval midgut (Sparks et al., PloS One, (2013) 8:5, e61190).

The discovery of RNA mediated interference (RNAi) has facilitated research to understand gene function and regulation. RNAi provides a silencing technique to deplete functional expression of targeted genes by degradation of mRNA into short RNAs. RNAi takes advantage of internal cellular defenses against the presence of dsRNA, which typically indicates an on-going viral infection. Double stranded RNAs (dsRNA) are cleaved by Dicer, a member of the RNase III superfamily of bidentate nucleases that are evolutionarily conserved in worms, flies, plants, fungi and mammals (Bernstein et al., Nature (2001) 409:6818, 363-66; Ketting et al., Genes Develop, (2001) 15:20, 2654-59). These 19-21 base pair short RNAs or siRNAs, unwind and together with RNA-induced silencing complex (RISC) associate with the complementary RNA. This RISC-RNA complex in conjunction with argonaute multi-domain protein containing an RNAse H like domain is responsible for target degradation and silencing the gene (Martinez et al., Cell, (2002) 110:5, 563-74; Bartel, Cell, (2004) 116:2, 281-97).

The major limiting factors for in vivo application of dsRNA mediated RNAi have been the cellular uptake of dsRNA, the method of delivery, and the stability of dsRNA after its delivery. Effective approaches for RNAi delivery—such as injecting the target organism, soaking the target, or feeding extracellular dsRNA (or intracellular dsRNA in a transgenic microbe) to the target—have been reported with varied success. Fire and colleagues first observed the phenomenon of RNAi by injecting dsRNA in the nematode, *Caenorhabditis elegans* (*C. elegans*) to deplete unc-22 gene generating twitching phenotypes (Fire et al., Nature, (1998) 391:6669, 806-11). Later, unc-22 depletion was accomplished in *C. elegans* by feeding *E. coli* inducing dsRNA (Timmons & Fire, Nature, (1998) 395:6705, 854). Subsequently RNAi was successfully performed in other animals such as *Drosophila melanogaster* (*D. melanogaster*) to downregulate the frizzled and frizzled 2 genes (Kennerdell & Carthew, Cell, (1998) 95:7, 1017-26). Clemens et al, used RNAi in *Drosophila* S2 tissue cultures cells to inhibit the expression of the DSOR1 (mitogen-activated protein kinase kinase, MAPKK) which prevented the activation of the downstream ERK-A (MAPK) in the insulin signal transduction pathway and vice versa (Clemens et al., Proc Nat'l Acad Sci USA, (2000) 97:12, 6499-6503).

Though lepidopteran insects have been resistant to RNAi, some successful dsRNA mediated RNAi instances have been observed in this class of insects. In one instance, aminopeptidase gene (slapn) dsRNA injected into the midgut of *Spodoptera litura* reduced its expression and susceptibility to Bt cry1C protein (Rajagopal et al., J Biol Chem, (2002) 277:49, 46849-51). Other studies demonstrated RNAi by feeding dsRNA either in a sucrose droplet to reduce the transcription of carboxylesterase gene (EposCXE1) in *Epiphyas postvittana*, or from plants engineered to produce dsRNA against cytochrome P450 gene (CYP6AE14) in *Helicoverpa armigera* (Turner et al., Insect Mol Biol, (2006) 15:3, 383-91; Mao et al., Nature Biotech, (2007) 25:11, 1307-13).

Disclosed herein, we describe various specifically designed RNAi examined in vivo in *L. dispar* larvae for efficiency in gene knock-down and depletion; several different delivery methods were also evaluated. Observations revealed that dsRNA synthesized to the midgut genes of *L. dispar* and delivered per os could suppress the expression of specifically targeted genes in vivo. RNA interference through feeding may be beneficial over other techniques, firstly due to the ease in feeding large number of insects inexpensively and secondly to preserve the sustainable farming practices.

SUMMARY OF THE INVENTION

One embodiment of the present invention provides a double-stranded ribonucleic acid (dsRNA) comprising a sense region with at least 95% sequence identity to any of SEQ ID NOs. 1-5 and an antisense region comprising a second sequence complementary to the sense region. In a particular embodiment, a dsRNA of the present invention has at least 99% or 100% sequence identity to any of SEQ ID NOs. 1-5. dsRNAs of the present invention can be expressed in a plant cell, for example a hardwood tree cell. In other embodiments, dsRNAs of the present invention are expressed in a bacterial or yeast cell. In still other embodiments, a dsRNA of the present invention can also contain a T7 RNA polymerase promoter sequence.

In another embodiment, the present invention provides a double-stranded ribonucleic acid (dsRNA) comprising a sense region comprising a sequence with at least 95% sequence identity to a portion of at least 19 consecutive nucleotides of any of SEQ ID NOs. 1-5 and an antisense region comprising a second sequence complementary to the sense region. dsRNAs of the present invention can be expressed in a plant cell, for example a hardwood tree cell. In other embodiments, dsRNAs of the present invention are expressed in a bacterial or yeast cell.

Also provided is an embodiment where a DNA molecule comprising a promoter functional in a host cell and a DNA encoding a dsRNA comprising a first region and a second region, wherein the first region comprises a sense region with at least 95% sequence identity to any of SEQ ID NOs. 1-5 and a second region complementary to the first region. In some embodiments of this invention, the host cell is a bacterial cell, a yeast cell or a plant cell.

Also provided herein are host cells comprising any one or more of the DNA molecules or dsRNA molecules described herein. In a particular example, such host cells are hardwood tree cells.

A further embodiment of the present invention comprises a transgenic plant cell, transgenic plant or transgenic seed comprising any dsRNA described herein, such as any one of SEQ ID NOs. 1-5. In some instances the plant cell, plant or seed of the present invention is a hardwood tree cell, hardwood tree, or hardwood tree seed.

In another embodiment of the present invention, the inventors provide a method of controlling L. dispar comprising applying one or more dsRNA molecules described herein to a plant on which one or more L. dispar insects feed and allowing the one or more insects to ingest an effective amount of the one or more dsRNA molecules, thereby controlling the one or more insects. In a particular embodiment of this method, the dsRNA molecule(s) applied to a plant is present in a transgenic bacterial cell. In one embodiment, the one or more dsRNA molecules applied to a plant comprise a first dsRNA molecule and a second dsRNA molecule, wherein the first dsRNA molecule comprises a sense region with at least 95% sequence identity to SEQ ID NO. 2 and an antisense region comprising a second sequence complementary to the sense region and wherein the second dsRNA molecule comprises a sense region with at least 95% sequence identity to SEQ ID NO. 3 and an antisense region comprising a second sequence complementary to the sense region.

An additional embodiment described herein provides a method of controlling L. dispar comprising, planting or growing a transgenic plant expressing one or more dsRNA molecules comprising all or an effective portion of any one of SEQ ID NOs. 1-5 and allowing one or more insects to ingest an effective amount of the one or more dsRNA molecules, thereby controlling the one or more insects. In a particular embodiment, the one or more dsRNA molecules comprise a first dsRNA molecule and a second dsRNA molecule, wherein the first dsRNA molecule comprises a sense region with at least 95% sequence identity to SEQ ID NO. 2 and an antisense region comprising a second sequence complementary to the sense region and wherein the second dsRNA molecule comprises a sense region with at least 95% sequence identity to SEQ ID NO. 3 and an antisense region comprising a second sequence complementary to the sense region.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the claims. Features and advantages of the present invention are referred to in the following detailed description, and the accompanying drawings of which:

FIG. 2A shows an analysis of RNAi depletion of specific gene targets and effects, or lack thereof, on body mass post ingestion. Third instar larvae were fed on dsRNA induced in bacterial culture indicated here as L4440 (control), Locus 22, Locus 365, Locus 28365, Locus 5421 and Locus 4413 for a period of 5 days following which the larvae were moved to AD. As a negative control, artificial diet was mixed with water prior to feeding the larvae. Body mass was measured on the thirteenth and eighteenth day after dsRNA feeding stopped. Results are from three biological replicates and error bars indicate SEM. FIG. 2B shows the results of quantitative RT-PCR analysis of transcript levels in L. dispar. cDNA of total RNA isolated from the gut tissue of L. dispar larvae fed on dsRNA inducing bacterial culture of Locus 22, Locus 365, Locus 28365, Locus 5421 and Locus 4413 was analyzed using qPCR. Larvae fed on L4440 empty vector served as control. 18s RNA was used as an internal standard to correct for differences in RNA recovery from tissues. Results are from three biological replicates, and error bars indicate SEM.

FIGS. 3A, 3B and 3C provide analysis of in vitro transcription of dsRNA. FIG. 3A shows fragments of Locus 22 (lane 2), Locus 365 (lane 3), Locus 28365 (lane 4), Locus 5421 (lane 5), and Locus 4413 (lane 6) obtained after re-amplifying the PCR products from genomic DNA amplification with primers that contained the T7 promoter sequence. PCR was performed with 2 different annealing Tm, 55° C. for 2 cycles and 65° C. for 30 cycles. The PCR products were confirmed by electrophoresis on 1% agarose and visualized by staining with Sybr Gold (Life Technologies) alongside a DNA ladder (Lane 1). FIG. 3B shows 2.5 µg of PCR product of Locus 22 (lane 2), Locus 365 (lane 3), Locus 28365 (lane 4), Locus 5421 (lane 5), or Locus 4413 (lane 6) flanked with converging T7 promoter sequence on each side was in vitro transcribed using T7 polymerase. dsRNA transcribed was confirmed by electrophoresis on 1% agarose and visualized by staining with Sybr Gold (Life technologies) alongside a DNA ladder (Lane 1). FIG. 3C shows LacZ gene PCR product (lane 2) and dsRNA (lane 3) transcribed was confirmed by electrophoresis on 1% agarose and visualized by staining with Sybr Gold (Life Technologies) alongside a DNA ladder (Lane 1).

FIG. 4A shows images taken 5 days after per os of feeding of dsRNA stopped. Control (panels a1-a2) were compared to Mock (panels b1-b4), Locus 22 (panels c1-c4), Locus 365 (panels d1-d4), Locus 28365 (panels e1-e4), Locus 5421 (panels f1-f4), Locus 4413 (panels g1-g4) or Loci 365+28365 (panels h1-h4). All images were measured to scale of 1 cm as indicated in panel a1. FIG. 4B shows analysis of RNAi depletion of specific gene targets and effects, or lack thereof, on body mass measured on the fifth and fifteenth day after feeding of dsRNA to the insects stopped. Results are from four biological replicates and error bars indicate variations in biological samples.

DETAILED DESCRIPTION OF THE INVENTION

Figure 1:
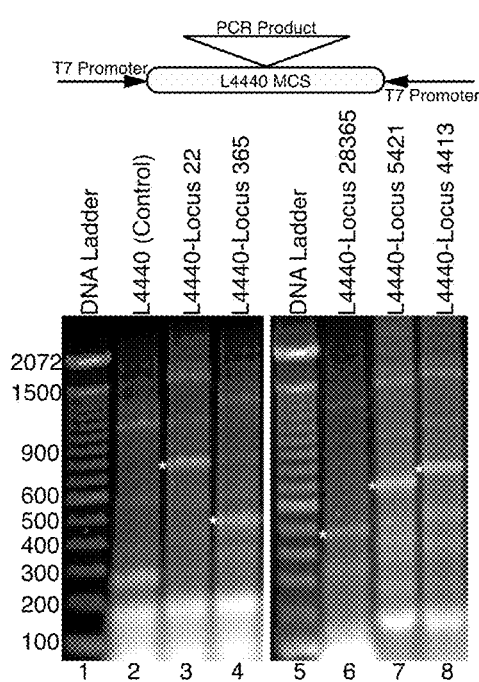
FIG. 1 provides analysis of dsRNA induced in the HT115 (DE3) bacterial strain. E. coli strain, HT115(DE3) was transformed with the L4440 plasmid containing regions of interest to express dsRNA for Loci 22, 365, 28365, 5421 and 4413 genes. Transformed bacteria were grown in NZCYM liquid media and induced with IPTG. Total nucleic acid was isolated from 2 ml of the induced culture using Trizol and treated with RQ1 DNase and RNaseA to remove DNA and single stranded RNA. 5 µg of the isolated nucleic acid samples was resolved by electrophoresis on 1% agarose and visualized by staining with SYBR GOLD (Life Technologies). Bands visualized and denoted by (*) indicate nucleic acids that are resistant to RNase and DNase treatment. DNA markers are included for comparison (lanes 1 and 5). The empty vector (L4440) transformed into HT115(DE3) served as a positive control (lane 2). Lanes 3, 4, 6, 7 and 8 represent loci 22, 365, 28365, 5421 and 4413 respectively (in the L4440 plasmid flanked by converging T7 promoters on each side). The increase in the observed molecular size of dsRNA to the cloned fragment is due the inclusion of the cloning region of plasmid L4440 between the two T7 promoters.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted.

Disclosed here are specific insect pest dsRNA constructs that target several *L. dispar* gene products. Using dsRNA inhibiting expression of the disclosed genes as a means of interfering with critical functions of the gene products, a novel method for pest management is disclosed, as well as new products to control certain insect pests.

Definitions

As used in the specification and claims, use of the singular "a", "an", and "the" include plural references unless the context clearly dictates otherwise.

The terms isolated, purified, or biologically pure as used herein, refer to material that is substantially or essentially free from components that normally accompany the referenced material in its native state.

The term "about" is defined as plus or minus ten percent of a recited value. For example, about 1.0 g means from a range of 0.9 g to 1.1 g.

The term "gene" refers to a DNA sequence involved in producing a RNA or polypeptide or precursor thereof. The polypeptide or RNA can be encoded by a full-length coding sequence or by intron-interrupted portions of the coding sequence, such as exon sequences.

The term "oligonucleotide" refers to a molecule comprising a plurality of deoxyribonucleotides or ribonucleotides. Oligonucleotides may be generated in any manner known in the art, including chemical synthesis, DNA replication, reverse transcription, polymerase chain reaction, or a combination thereof. In one embodiment, the present invention embodies utilizing the oligonucleotide in the form of dsRNA as means of interfering with a critical developmental or reproductive process that leads to control. Inasmuch as mononucleotides are synthesized to construct oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide, which is capable of acting as a point of initiation of synthesis when placed under conditions in which primer extension is initiated. An oligonucleotide "primer" may occur naturally, as in a purified restriction digest or may be produced synthetically.

A primer is selected to be "substantially complementary" to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficiently complementary with the sequence of the template to hybridize and thereby form a template primer complex for synthesis of the extension product of the primer.

As used herein, "dsRNA" refers to double-stranded RNA that comprises a sense and an antisense portion of a selected target gene (or sequences with high sequence identity thereto so that gene silencing can occur), as well as any smaller double-stranded RNAs formed therefrom by RNAse or dicer activity. Such dsRNA can include portions of single-stranded RNA, but contains at least 19 nucleotides double-stranded RNA. In one embodiment of the invention, a dsRNA comprises a hairpin RNA which contains a loop or spacer sequence between the sense and antisense sequences of the gene targeted, preferably such hairpin RNA spacer region contains an intron, particularly the rolA gene intron (Pandolfini et al., 2003, BioMedCentral (BMC) Biotechnology 3:7 (www.biomedcentral.com/1472-6750/3/7)), the dual orientation introns from pHellsgate 11 or 12 (see WO 02/059294 and SEQ ID NO: 25 and 15 therein) or the pdk intron (*Flaveria trinervia* pyruvate orthophosphate dikinase intron 2; see WO99/53050).

Included in this definition are "siRNAs" or small interfering (double-stranded) RNA molecules of 16-30 bp, 19-28 bp, or 21-26 bp, e.g., such as the RNA forms that can be created by RNAseIII or dicer activity from longer dsRNA. siRNAs as used herein include any double-stranded RNA of 19 to 26, or 21 to 24 basepairs that can interfere with gene expression when present in a cell wherein such gene is expressed. siRNA can be synthetically made, expressed and secreted directly from a transformed cell or can be generated from a longer dsRNA by enzymatic activity. These siRNAs can be blunt-ended or can have overlapping ends. Also modified microRNAs comprising a portion of a *L. dispar* target gene and its complementary sequence are included herein as dsRNAs.

In one embodiment of this invention, dsRNA is used to control *L. dispar* without such dsRNA being co-delivered with a transfection-promoting agent, although in some embodiments the dsRNA of the invention can be provided in a solution with a transfection-promoting agent. In one embodiment of the invention, the dsRNA is expressed in a plant to be protected, or in microorganisms which can be sprayed on plants to be protected. A "transfection promoting agent", as used herein, refers to a lipid-containing material that secures uptake into a cell of a dsRNA (hence crossing the cell membrane), particularly liposomes. Examples of such agents are described in published PCT patent application WO 03/004644.

The term "chimeric" when referring to a gene or DNA sequence is used to refer to a gene or DNA sequence comprising at least two functionally relevant DNA fragments (such as promoter, 5'UTR, coding region, 3'UTR, intron) that are not naturally associated with each other, such as a fusion of functionally relevant DNA fragments from different sources to form a plant-expressible chimeric gene expressing a dsRNA targeting a *L. dispar* gene.

Sequences or parts of sequences which have "high sequence identity", as used herein, refers to the number of positions with identical nucleotides divided by the number of nucleotides in the shorter of the sequences, being higher than 95%, higher than 96%, higher than 97%, higher than 98%, higher than 99%, or between 96% and 100%. A target gene, or at least a part thereof, as used herein, preferably has high sequence identity to the dsRNA of the invention in order for efficient gene silencing to take place in the target pest. Identity in sequence of the dsRNA or siRNA with a part of the target gene RNA is included in the current invention but is not necessary.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch, J Mol Biol, (1970) 48:3, 443-53). A computer-assisted sequence alignment can be conveniently performed using a standard software program such as GAP which is part of the Wisconsin Package Version 10.1 (Genetics Computer Group, Madison, Wis., USA) using the default scoring matrix with a gap creation penalty of 50 and a gap extension penalty of 3.

For the purpose of the invention, the "complement of a nucleotide sequence X" is the nucleotide sequence which would be capable of forming a double-stranded DNA or RNA molecule with the represented nucleotide sequence, and which can be derived from the represented nucleotide sequence by replacing the nucleotides by their complementary nucleotide according to Chargaff's rules (A< >T; G< >C; A< >U) and reading in the 5' to 3' direction, i.e., in opposite direction of the represented nucleotide sequence.

In one embodiment of the invention, sense and antisense RNAs can be separately expressed in vitro or in host cells, e.g., from different chimeric gene constructs using the same or a different promoter, or from a construct containing two convergent promoters in opposite orientation. These sense and antisense RNAs which are formed, e.g., in the same host cells, can then combine to form dsRNA. It is clear that whenever reference is made herein to a dsRNA chimeric gene or a dsRNA molecule that such dsRNA formed, in vivo or in vitro, from sense and antisense RNA produced separately is also included. Also synthetically made dsRNA annealing RNA strands are included herein when the sense and antisense strands are present together.

A dsRNA "targeting" a *L. dispar* gene, as used herein, refers to a dsRNA that is designed to be identical to, or have high sequence identity to, one or more endogenous *L. dispar* mRNAs (the target genes), and as such is designed to silence such gene upon application to such insect or to plants fed on by such insects. One dsRNA can target one or several homologous target genes in one insect or one or several homologous target genes in different insects which can feed on the same host plant. In one embodiment of the invention, the gene target is any one represented by Locus 22, Locus 365, Locus 28365, Locus 5421, Locus 4413 or a combination thereof.

"Insecticidal activity" of a dsRNA, as used herein, refers to the capacity to obtain mortality in insects when such dsRNA is fed to insects, preferably by expression in a recombinant host such as a plant, which mortality is significantly higher than a negative control (using a non-insect dsRNA or buffer). "Insect-control" of a dsRNA, as used herein, refers to the capacity to inhibit the insect development, fertility, inhibition of pheromone production, or growth in such a manner that the insect population provides less damage to a plant, produces fewer offspring, are less fit or are more susceptible to predator attack, or that insects are even deterred from feeding on such plant.

"Substantially identical" as used herein, means there is a very high degree of homology (preferably 100% sequence identity) between the inhibitory dsRNA and the corresponding part of the target gene. However, dsRNA having greater than 90% or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base pair random mismatches between the RNA and the target gene.

As used herein, the term "LacZ dsRNA" refers to a control dsRNA construct targeting a LacZ sequence. The LacZ protein (lacZ) is commonly used as a reporter gene in prokaryotic systems.

The term "corresponds to" as used herein means a polynucleotide sequence homologous to all or a portion of a reference polynucleotide sequence, or a polypeptide sequence that is identical to a reference polypeptide sequence. In contradistinction, the term "complementary to" is used herein to mean that the complementary sequence is homologous to all or a portion of a reference polynucleotide sequence. For example, the nucleotide sequence "TATAC" corresponds to a reference sequence "TATAC" and is complementary to a reference sequence "GTATA". An "RNA form" of a DNA sequence, as used herein is the RNA sequence of said DNA, so the same sequence but wherein the T nucleotide is replaced by a U nucleotide.

An "effective amount" is an amount sufficient to effect desired beneficial or deleterious results. An effective amount can be administered in one or more administrations. In terms of treatment, an "effective amount" is that amount sufficient to make the target pest non-functional by causing an adverse effect on that pest, including (but not limited to) physiological damage to the pest; inhibition or modulation of pest growth; inhibition or modulation of pest reproduction; or death of the pest. In one embodiment of the invention, a dsRNA containing solution is fed to a target insect wherein critical developmental and/or reproductive functions of said insect are disrupted as a result of ingestion.

The term "solvent" includes any liquid that holds another substance in solution. Examples of solvents include but are not limited to water and organic solvents such as acetone, ethanol, dimethyl sulfoxide (DMSO), and dimethylformamide (DMF).

The term "phagostimulant" refers to any substance that will entice the insect to ingest the dsRNA. For insects, suitable phagostimulants include but are not limited to syrups, honey, aqueous solutions of sucrose, artificial sweeteners such as sucralose, saccharin, and other artificial sweeteners, and amino acids.

Double-Stranded RNA and RNA Interference

Since its inception, RNAi has proved to be a potent tool to study gene function and regulation. With the advent of bioinformatics coupled with next-generation high throughput sequencing has unveiled an array of transcriptomic data available for a wide range of species at different stages of development and tissues. Disclosed herein is a collection of *L. dispar* transcripts used in the dsRNA mediated depletion of functional expression target genes for the development of biomolecular pest control. To attain an effective RNAi response in the biocontrol of pests, an accurate and precise mode of dsRNA delivery, efficient uptake and dsRNA stability are of utmost consideration.

The process of selecting the regions and gene targets utilized in developing the present invention was facilitated by the recent availability of the transcriptomic profile for gypsy moth (Sparks & Gundersen-Rindal, Viruses, (2011) 3:12, 2339-50; Sparks et al., PloS One, (2013) 8:5, e61190). RNAi studies showing successful depletion of aminopeptidase gene (slapn) and vitellogenin receptor (VgR) in *Spodoptera litura* (Lepidoptera: Noctuidae) by dsRNA in lepidoteran insects have been reported (Rajagopal et al., J Biol Chem, (2002) 277:49, 46849-51; Shu et al., Insect Mol Biol, (2011) 20:1, 61-73). In addition to analyzing RNAi targeting the *L. dispar* homologs of slapn and vitellogenin, we also analyzed the effects of inhibitory dsRNA on an *L. dispar* homolog of Osiris 9 (a gene of unknown function) and two genes termed "locus 365" and "locus 28365" (currently of unknown function and thought to be unique to *L. dispar*).

Sequences homologous to the *C. elegans* systemic RNA interference deficient-1 (sid-1) gene responsible for the systemic spread of dsRNAs, have been identified in *A. mellifera* and *B. mori* (Winston et al., Science, (2002) 295:5564, 2456-59; Honeybee Genome Sequencing Consortium, Nature, (2006) 443:7114, 931-49). A similar homologue of the *B. mori* Sid-1 sequence in the transcriptome of *L. dispar* has been reported (Sparks et al., PloS One, (2013) 8:5, e61190), suggesting that ingestion of dsRNA per os could be a viable route of delivery for *L. dispar*. While any method capable of delivering an effective amount of dsRNA to target animals known in the art (including microinjection to deliver to a precise location in the animal, soaking and ingestion) can be utilized to practice the present invention, demonstrated in specific embodiments herein are application to a target insect via food and liquid of both dsRNA expressed in a transgenic bacterial cell (Timmons & Fire, Nature, (1998) 395:6705, 854) and in vitro synthesized dsRNA per os (i.e., orally).

Zhang et al., examined the use of chitosan/dsRNA nanoparticle mediated RNAi for silencing the two chitin synthase genes, AgCHS1 and AgCHS2 (Zhang et al., Insect Mol Biol, (2010) 19:5, 683-93). These nanoparticles are delivered into the insect by ingestion. The novelty of this technique is the formation of nanoparticles that stabilize the dsRNA molecules. This is important for the delivery process and enhancing the efficacy of RNAi. We tested this method of dsRNA delivery in larvae as well as IPLB-LdEp gypsy moth tissue culture cells with partial success in tissue culture (data not shown).

Preferably, the dsRNAs to be used in this invention target at least one *L. dispar* gene portion of at least 19 consecutive nucleotides occurring in identical sequence or with high sequence identity in *L. dispar*. In one embodiment of this invention, such dsRNAs do not silence genes of a plant host, or of other non-target animals, such as *L. dispar* predators or animals such as reptiles, amphibians, birds, or mammals. Levels of homology between sequences of interest can be analyzed in available databases, e.g., by a BLAST search (see also www.ncbi.nlm.nih.gov/BLAST) or by hybridization with existing DNA libraries of representative non-target organisms. In one embodiment of this invention, the dsRNA or siRNA of the invention corresponds to an exon in a target gene.

As used herein, nucleotide sequences of RNA molecules can be identified by reference to DNA nucleotide sequences of the sequence listing. However, the person skilled in the art will understand whether RNA or DNA is meant depending on the context. Furthermore, the nucleotide sequence is identical between the types of polynucleotides except that the T-base is replaced by uracil (U) in RNA molecules.

In some embodiments, the length of the first (e.g., sense) and second (e.g., antisense) nucleotide sequences of the dsRNA molecules of the invention can vary from about 10 nucleotides (nt) up to a length equaling the length in nucleotides of the transcript of the target gene. The length of the first or second nucleotide sequence of the dsRNA of the invention can be at least 15 nt, or at least about 20 nt, or at least about 50 nt, or at least about 100 nt, or at least about 150 nt, or at least about 200 nt, or at least about 400 nt, or at least about 500 nt. If not all nucleotides in a target gene sequence are known, it is preferred to use such portion for which the sequence is known and which meets other beneficial requirements of the invention.

It will be appreciated that the longer the total length of the first (sense) nucleotide sequence in the dsRNA of the invention is, the less stringent the requirements for sequence identity between the total sense nucleotide sequence and the corresponding sequence in the target gene becomes. The total first nucleotide sequence can have a sequence identity of at least about 75% with the corresponding target sequence, but higher sequence identity can also be used such as at least about 80%, at least about 85%, at least about 90%, at least about 95%, about 100%. The first nucleotide sequence can also be identical to the corresponding part of the target gene. However, it is advised that the first nucleotide sequence includes a sequence of 19 or 20, or about 19 or about 20 consecutive nucleotides, or even of about 50 consecutive nucleotides, or about consecutive 100 nucleotides, or about 150 consecutive nucleotides with only one mismatch, preferably with 100% sequence identity, to the corresponding part of the target gene. For calculating the sequence identity and designing the corresponding first nucleotide sequence, the number of gaps should be minimized, particularly for the shorter sense sequences.

The length of the second (antisense) nucleotide sequence in the dsRNA of the invention is largely determined by the length of the first (sense) nucleotide sequence, and may correspond to the length of the latter sequence. However, it is possible to use an antisense sequence which differs in length by about 10% without any difficulties. Similarly, the nucleotide sequence of the antisense region is largely determined by the nucleotide sequence of the sense region, and may be identical to the complement of the nucleotide sequence of the sense region. Particularly with longer antisense regions, it is however possible to use antisense sequences with lower sequence identity to the complement of the sense nucleotide sequence, such as at least about 75% sequence identity, or least about 80%, or at least about 85%, more particularly with at least about 90% sequence identity, or at least about 95% sequence to the complement of the sense nucleotide sequence. Nevertheless, it is advised that the antisense nucleotide sequence always includes a sequence of 19 or 20, about 19 or about 20 consecutive nucleotides, although longer stretches of consecutive nucleotides such as about 50 nucleotide, or about 100 nucleotides, or about 150 nucleotides with no more than one mismatch, preferably with 100% sequence identity, to the complement of a corresponding part of the sense nucleotide sequence can also be used. Again, the number of gaps should be minimized, particularly for the shorter (19 to 50 nucleotides) antisense sequences.

In one embodiment of the invention, the DNA molecules according to the invention can comprise a DNA region encoding a spacer between the DNA region encoding the first and second nucleotide sequences. As indicated in WO 99/53050 the spacer may contain an intron to enhance gene silencing. A particularly preferred intron functional in cells of plants is the pdk intron (*Flaveria trinervia* pyruvate orthophosphate dikinase intron 2; see WO99/53050), the delta 12 desaturase intron from *Arabidopsis* (Smith et al., Nature, (2000) 407:319-20) or the intron of the rolA gene (Magrelli et al., Science (1994) 266:1986-1988; Spena and Langenkemper, Genet Res, (1997) 69:11-15).

In one embodiment of the invention, a dsRNA molecule may further comprise one or more regions having at least 94%, at least 95%, at least 96%, at least 97%, at least 98%, or at least 99%, sequence identity to regions of at least 19 consecutive nucleotides from the sense nucleotide sequence of the target gene, different from the at least 19 consecutive nucleotides as defined in the first region, and one or more regions having at least 94%, at least 95%, at least 96%, at least 97%, at least 98%, or at least 99%, sequence identity to at least 19 consecutive nucleotides from the complement of the sense nucleotide sequence of the target gene, different from the at least 19 consecutive nucleotides as defined in the second region, wherein these additional regions can base-pair amongst themselves.

In particular embodiments, a dsRNA molecule of the present invention comprises a first (sense) strand that is 90%-100% identical to any of SEQ ID NOs. 1-5. For example, a dsRNA molecule that has 90%, 91%, 92%, 93%, 94%, 95%, 96%, 97%, 98%, 99%, 100% sequence identity to any of SEQ ID NOs. 1-5. One of skill in the art will recognize that these whole number percentages encompass any portion or fraction of a percentage between 90% and 100%.

Transgenic Plants and Plant Cells

One embodiment of the present invention provides a plant or cell comprising one or more inhibitory dsRNAs specific for one or more mRNAs of one or more *L. dispar* genes. Inhibitory RNAs specific for one or more mRNAs means that the inhibitory RNA down-regulates the expression, or translation, of a specific mRNA. The inhibitory RNA can be single- or double-stranded or a combination thereof. For example, the present disclosure provides transgenic plants that express one or more inhibitory RNAs that down regulate expression, or translation, of one or more target genes when the one or more inhibitory RNAs are absorbed or ingested by a target insect (e.g., *L. dispar*).

Another embodiment provides a transgenic plant that comprises inhibitory RNA that down regulates 3, 4, 5, 6, 7, 8, 9, 10, 11, 12, 13, 14, 15, 16, 17, 18, 19, 20, or more *L. dispar* genes. Thus, the present disclosure provides transgenic plants and transgenic plant material that are resistant to disease caused by *L. dispar*.

Another embodiment provides a transgenic plant or transgenic cell containing or expressing one or more inhibitory nucleic acids specific for at least a portion of a nucleic acid encoding one or more *L. dispar* genes. The inhibitory nucleic acid is typically a small inhibitory RNA or microRNA that is specific for mRNA encoding a *L. dispar* gene involved in growth, general health, fecundity, or reproduction. In some instances, the function of the target gene (or the protein encoded by the gene) is not known.

It will be appreciated by one of skill in the art that an inhibitory nucleic acid can be RNA, DNA, or a combination thereof. Additionally, the inhibitory nucleic acid can be single or multi-stranded and can be anti-sense or enzymatic. In one embodiment, an inhibitory nucleic acid interferes with, inhibits, or reduces the translation of a target mRNA. For example, an inhibitory nucleic acid can bind to a target mRNA and induce or promote the degradation of the target mRNA or physically prevent the cellular translational machinery from translating the target mRNA into a functional protein.

In some embodiments, a dsRNA chimeric gene, encoding a dsRNA targeting any of the genes disclosed herein, can be stably inserted in a conventional manner into the genome of a single plant cell, and the so-transformed plant cell can be used in a conventional manner to produce a transformed (i.e., transgenic) plant that has increased insect resistance. In this regard, a disarmed Ti-plasmid, containing the dsRNA chimeric gene, in *Agrobacterium tumefaciens* can be used to transform the plant cell, and thereafter, a transformed plant can be regenerated from the transformed plant cell using the procedures described in the art, for example, in EP 0116718, EP 0270822, PCT publication WO 84/02913 and published European Patent application ("EP") 0242246. Preferred Ti-plasmid vectors each contain the dsRNA chimeric gene between the border sequences, or at least located to the left of the right border sequence, of the T-DNA of the Ti-plasmid. Of course, other types of vectors can be used to transform the plant cell, using procedures such as direct gene transfer (as described, for example in EP 0233247), pollen mediated transformation (as described, for example in EP 0270356, PCT publication WO 85/01856, and U.S. Pat. No. 4,684,611), plant RNA virus-mediated transformation (as described, for example in EP 0 067 553 and U.S. Pat. No. 4,407,956), liposome-mediated transformation (as described, for example in U.S. Pat. No. 4,536,475), and other methods such as the methods for transforming certain lines of corn (e.g., U.S. Pat. No. 6,140,553; Fromm et al., Bio/Technology (1990) 8, 833-839); Gordon-Kamm et al., The Plant Cell, (1990) 2, 603-618) and rice (Shimamoto et al., Nature, (1989) 338, 274-276; Datta et al., Bio/Technology, (1990) 8, 736-740) and the method for transforming monocots generally (PCT publication WO 92/09696). For cotton transformation, the method described in PCT patent publication WO 00/71733 can be used. For soybean transformation, reference is made to methods known in the art, e.g., Hinchee et al. (Bio/Technology, (1988) 6, 915) and Christou et al. (Trends Biotech, (1990) 8, 145) or the method of WO 00/42207.

The resulting transgenic plant can be used in a conventional plant breeding scheme to produce more transgenic plants with the same characteristics, or to introduce the dsRNA chimeric gene in other varieties of the same or related plant species. Seeds, which are obtained from the transformed plants, contain the dsRNA gene as a stable genomic insert. Plants comprising a dsRNA in accordance with the invention include plants comprising, or derived from, root stocks of plants comprising the dsRNA chimeric gene of the invention, e.g., fruit trees or ornamental plants. Hence, any non-transgenic grafted plant parts inserted on a transformed plant or plant part are included in the invention since the RNA interference signal is transported to these grafted parts and any insects feeding on such grafted plant are similarly affected by the dsRNA or siRNA of the invention.

A DNA encoding a dsRNA is typically inserted in a plant cell genome so that this DNA is downstream (i.e., 3') of, and operably linked to, a plant-expressible promoter which can direct expression in plant cells. This is preferably accomplished by inserting a dsRNA chimeric gene into the plant cell genome, particularly in the nuclear or plastid (e.g., chloroplast) genome. Also, in a dsRNA chimeric gene of the invention a nuclear localization signal can be added as described in published US patent application 20030180945.

A 'plant-expressible promoter' as used herein refers to a promoter that ensures expression of a dsRNA of the invention in a plant cell. Examples of promoters directing constitutive expression in plants are known in the art and include: the strong constitutive 35S promoters (the "35S promoters") of the cauliflower mosaic virus (CaMV), e.g., of isolates CM 1841 (Gardner et al., Nucleic Acids Res, (1981) 9, 2871-2887), CabbB-S (Franck et al., Cell (1980) 21, 285-294) and CabbB-JI (Hull and Howell, Virology, (1987) 86, 482-493); promoters from the ubiquitin family (e.g., the maize ubiquitin promoter of Christensen et al., Plant Mol Biol, (1992) 18, 675-689), the gos2 promoter (de Pater et al., The Plant J (1992) 2, 834-844), the emu promoter (Last et al., Theor Appl Genet, (1990) 81, 581-588), actin promoters such as the promoter described by An et al. (The Plant J, (1996) 10, 107), the rice actin promoter described by Zhang et al. (The Plant Cell, (1991) 3, 1155-1165); promoters of the Cassava vein mosaic virus (WO 97/48819, Verdaguer et al. (Plant Mol Biol, (1998) 37, 1055-1067), the pPLEX series of promoters from Subterranean Clover Stunt Virus (WO 96/06932, particularly the S4 or S7 promoter), an alcohol dehydrogenase promoter, e.g., pAdh1S (GenBank accession numbers X04049, X00581), and the TR1' promoter and the TR2' promoter (the "TR1' promoter" and "TR2' promoter", respectively) which drive the expression of the 1' and 2' genes, respectively, of the T-DNA (Velten et al., EMBO J, (1984) 3, 2723-2730).

Alternatively, a plant-expressible promoter can be a tissue-specific promoter, i.e., a promoter directing a higher level of expression in some cells or tissues of the plant, e.g., in green tissues (such as the promoter of the PEP carboxylase). The plant PEP carboxylase promoter (Pathirana et al., Plant J, (1997) 12:293-304) has been described to be a strong promoter for expression in vascular tissue and is useful in one embodiment of the current invention. Alternatively, a plant-expressible promoter can also be a wound-inducible promoter, such as the promoter of the pea cell wall invertase gene (Zhang et al., Plant Physiol, (1996) 112:1111-1117). A 'wound-inducible' promoter as used herein means that upon wounding of the plant, either mechanically or by insect feeding, expression of the coding sequence under control of the promoter is significantly increased in such plant. These plant-expressible promoters can be combined with enhancer elements, they can be combined with minimal promoter elements, or can comprise repeated elements to ensure the expression profile desired.

Elements which can be used to increase expression in plant cells can be: an intron at the 5' end or 3' end of the chimeric gene, or in the coding sequence of the chimeric dsRNA gene (such as between the region encoding the sense and antisense portion of the dsRNA), e.g., the hsp70 intron, besides promoter enhancer elements, duplicated or triplicated promoter regions, 5' leader sequences different from another transgene or different from an endogenous (plant host) gene leader sequence, 3' trailer sequences different from another transgene used in the same plant or different from an endogenous (plant host) trailer sequence.

A dsRNA chimeric gene of the present invention can be inserted in a plant genome so that the inserted gene part is upstream (i.e., 5') of suitable 3' end transcription regulation signals (i.e., transcript formation and polyadenylation signals). This is preferably accomplished by inserting the dsRNA chimeric gene in the plant cell genome. Preferred polyadenylation and transcript formation signals include those of the nopaline synthase gene (Depicker et al., J. Molec Appl Gen, (1982) 1, 561-573), the octopine synthase gene (Gielen et al., EMBO J, (1984) 3:835-845), the SCSV or the Malic enzyme terminators (Schunmann et al., Plant Funct Biol, (2003) 30:453-460), and the T-DNA gene 7 (Velten and Schell, Nucleic Acids Res, (1985) 13, 6981-6998), which act as 3'-untranslated DNA sequences in transformed plant cells.

In some instances a transgenic plant of the present invention is a hardwood tree. In other embodiments, transgenic plant cells, plant seeds, or plant tissues of the present invention can be from a hardwood tree. Non-limiting examples of such trees include Alder (*Alnus* spp), American chestnut (*Castanea dentata*), Apple (*Malus* spp.), Aspen (*Populus* spp.), Basswood (*Tilia* spp.), Beech (*Fagus* spp.), Birch (*Betula* spp., *Betula papyrifera, Betula alleghaniensis, Betula lenta*), Box Elder (*Acer negundo*), Boxwood (*Buxus sempervirens*), Buckeye (*Aesculus* spp), California bay laurel (*Umbellularia californica*), Cherry (*Prunus* spp.), Cottonwood (*Populus deltoids, Populus fremontii, Populus nigra*), Cucumber tree (*Magnolia acuminata*), Ebony (*Diospyros* spp.), Elm (*Ulmus* spp.), *Eucalyptus* spp., European crabapple (*Malus sylvestris*), European pear (*Pyrus communis*), Hackberry (*Celtis occidentalis*), Hawthorn (*Crataegus* spp.), Hickory (*Carya* spp.), Hornbeams and Hophornbeams (*Carpinus* spp., *Ostrya* spp.), Ironwoods (*Shorea* spp., *Carpinus* spp., *Casuarina* spp, *Copaifera* spp., *Guaiacum* spp., *Hopea* spp., *Krugiodendron ferreum, Lyonothamnus floribundus.* etc.), Lacewoods (*Cardwellia sublimis, Platanus* spp.), Mahogany (*Swietenia* spp., *Melia* spp., *Carapa* spp., *Khaya* spp., *Toona* spp., *Entandrophragma* spp., *Chukrasia* spp., *Cedrela* spp., *Guarea* spp.), Maple (*Acer* spp.), Marblewood (*Marmaroxylon racemosum*), Oak (*Quercus* spp), Olive (*Olea* spp.), Poplar (*Populus* spp., *Liriodendron tulipifera*), Redheart (*Erythroxylon mexicanum*), Sweetgum (*Liquidambar styramflua*), Sandalwood (*Santalum* spp.), Sassafras (*Sassafras* spp.), Southern *sassafras* (*Atherosperma moschatum*), Satinwood (*Brosimum rubescens*), Silky oak (*Grevillea robusta*), Spanish elm (*Cordia alliodora*), Teak (*Tectona grandis*), Tupelo (*Nyssa* spp.), Turpentine (*Syncarpia glomulifera*), Walnut (*Juglans* spp.) Willow (*Salix* spp.), etc. One of skill in the art will recognize that this list provides exemplary organisms and that other hardwood trees, hardwood tree cells, hardwood tree seeds, and hardwood tree tissues can be constructed to express dsRNAs of the present invention. Preferably, such species will be ones subject to predation by *L. dispar.*

In some instances a transgenic plant of the present invention is a non-hardwood tree or shrub. In other embodiments, transgenic plant cells, plant seeds, or plant tissues of the present invention can be from a non-hardwood tree or shrub. Non-limiting examples of such trees and shrubs include, but are not limited to Hemlocks (*Tsuga* spp.), Junipers (*Juniperus* spp.), Pines (*Pinus* spp.), Spruce (*Picea* spp.), Tamarack (*Larix laricina*), Witch Hazel (*Hamamelis* spp.), etc. One of skill in the art will recognize that this list provides exemplary organisms and that other trees or shrubs, tree or shrub cells, tree or shrub seeds, and tree or shrub tissues can be constructed to express dsRNAs of the present invention. Preferably, such species will be ones subject to predation by *L. dispar.*

A dsRNA chimeric gene of the present invention can optionally be inserted in a plant genome as a hybrid gene, containing several dsRNA regions which target different genes. For example, a dsRNA chimeric gene can have dsRNA regions targeting 2, 3, 4, 5, 6, 7, 8, 9, 10, 11, 12, 13, 14, 15, 16, 17, 18, 19, 20 or more genes from *L. dispar*, an additional pest species, or a combination thereof. In some embodiments, a dsRNA chimeric gene of the present invention can contain several dsRNA regions which target different portions of the same gene, or target different alleles of the same gene. Also, it is convenient to include in the transforming DNA of the invention also a selectable or scorable marker gene, such as the bar, epsps or the neo gene, so that transformed plants can easily be selected by application of glufosinate, glyphosate or kanamycin, respectively, as is well known in the art. Advantageously, the plants or seeds of the invention also comprise a glufosinate or glyphosate tolerance gene besides the dsRNA chimeric gene of the invention, so that plants can be selected using application of the relevant herbicide (glufosinate or glyphosate).

Although plant delivery of a dsRNA is an embodiment of this invention, in accordance with this invention, application of the dsRNA of the invention can be done in several ways, and need not be by way of a plant expressing a dsRNA. Any method of delivery of dsRNA not contained in a plant cell is included herein, e.g., in vitro or in vivo produced dsRNA applied to an insect diet or feed, or microbially- or yeast-expressed dsRNA. dsRNA can be applied on plants on which *Lymantria dispar* feeds by spraying a solution of microbial/yeast spores/cells comprising the dsRNA of the invention. dsRNA species of the present invention can be applied on plants by spraying a culture, culture extract, culture supernatant, or a combination thereof, where the sprayed material comprises a microbe-expressed dsRNA. Thus, the present invention includes microbes comprising genetic elements allowing for the expression of any of the dsRNA species described herein.

In particular embodiments, the present invention provides a composition having an inhibitory nucleic acid specific for an mRNA or fragment thereof represented by one or more of SEQ ID NOs. 1-5 or a fragment or homologue thereof. Typically, dsRNAs of the present invention are provided to a target insect pest in an amount sufficient to inhibit production of the polypeptide encoded by one or more of the full-length genes targeted by SEQ ID NOs. 1-5 or homologues and alleles thereof. For example when *L. dispar* is feeding on a plant or cell expressing, or containing, or coated with an inhibitory nucleic acid, the insect ingests a sufficient level of dsRNA of SEQ ID NOs. 1-5 to result in a phenotypic effect. In particular embodiments, a combination of two or more dsRNAs of SEQ ID NOs. 1-5 are combined in a single insecticidal composition, for example a combination of dsRNA comprising SEQ ID NO. 2 and SEQ ID NO. 3. In addition to an inhibitory nucleic acid, an insecticidal composition of the present invention can contain one or more phagostimulants, pesticides, fungicides, or combinations thereof. The composition can be formulated to be coated to be coated on a plant, plant part, or seed. In certain aspects the inhibitory nucleic acid is combined with one or more excipients, buffering agents, carriers, etc. excipients, buffering agents, and carriers are well known in the art.

Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars and starches.

The coating can be formulated as a spray or dip so that the inhibitory nucleic acids remain on the plant material and remain able to inhibit target protein expression in L. dispar as the plant matures and develops. For example, the seed of a plant can be coated with a composition comprising an amount of one or more of the disclosed inhibitory nucleic acids effective to inhibit or reduce nematode disease in the plant in combination with an excipient.

Having described the invention in general, below are examples illustrating the generation and efficacy of the invention. Neither the examples, nor the general description above should be construed as limiting the scope of the invention.

EXAMPLES

Rearing L. dispar and M. sexta:

All L. dispar and M. sexta larvae used for this study were reared from single egg masses to reduce variability. L. dispar (Lepidoptera: Erebidae) eggs were acquired from USDA/APHIS, Otis ANGB, MA. The larvae were then reared to the third instar stage on artificial diet consisting of wheat germ, USDA vitamin mix, casein, wesson salts, sorbic acid, methyl paraben, and agar (Bell et al., in Doane & McManus, Technical Bulletin, United States Department of Agriculture 1584, (1981), 599-633) in 180-ml plastic cups. Larvae were staged by rearing in groups of approximately 50 individuals in 180-ml plastic cups until head capsule formation was observed signifying entry into the larval molt to third instar. M. sexta eggs were reared on tobacco hornworm (THW) diet strips (Martin, Biol Control, (2004) 29:1, 109-14; Martin & Blackburn, Biol Control, (2007) 42:2, 226-32) in a petri dish at 24° C. The emerging larvae were then moved to fresh diet strips placed on a raised mesh in pyrex containers. Larval molt to third instar was confirmed and these larvae were selected for RNAi.

Gene Selection and Analysis of dsRNA Induced in Bacteria.

Systemic RNAi transmitted through bacterial expression of dsRNA is a commonly used protocol in C. elegans (Timmons & Fire, Nature, (1998) 395:6705, 854; Kamath et al., Genome Biol, (2001) 2:1, RESEARCH0002). This technique uses the insertion of a fragment of a gene of interest for depletion in the multiple cloning site (MCS) of the L4440 plasmid vector between two converging T7 promoters. This cloned construct is transformed into HT115(DE3) E. coli strain for induction of dsRNA in the presence of isopropyl-b-d-thiogalactopyranoside (IPTG). The lack of RNase III, a double stranded RNA specific RNase makes this bacterial strain an ideal choice for dsRNA expression.

Genes were selected from the transcriptomic profiles of L. dispar midgut and Blasted against human and other animals for homology. Table 1 describes the best homolog identified in the NR protein sequence database for the associated transcript. Only genes that were strictly specific to L. dispar were selected from the high, mid and low quality tiers from the reported profiles (Sparks et al., PloS One, (2013) 8:5, e61190). While a total of 10 genes were initially analyzed, only five were selected for further analysis. These were: "locus 22", or the aminopeptidase N1 (APN1) gene which was identified as the Cry1Ac endotoxin of Bt receptor in L. dispar (Garner et al., Insect Biochem Mol Biol, (1999) 29:6, 527-35); "locus 5421", or the Osiris 9 gene, a gene of unknown function that is syntenic between B. mori and Drosophila (Suetsugu et al., G3 (Bethesda, Md.), (2013) 3:9, 1481-92; Shah et al., G3 (Bethesda, Md.), (2012) 2:2, 313-19) and displayed homology to the transcriptome profile of L. dispar; two genes known only as "locus 365" and "locus 28365" that are apparently unique to L. dispar; and "locus 4413", or the vitellogenin gene, a gene important for egg yolk precursor protein in insect females.

TABLE 1

Potential L. dispar target genes

| Locus No. | Size (bp) | Gene Name/Homology |
|---|---|---|
| Locus 3 | 500 | gb\|AAL26894.1\|aminopeptidase N3 [L. dispar] |
| Locus 22 | 500 | gb\|AAD31183.1\|AF126442_1 aminopeptidase N 1 [L. dispar] |
| Locus 536 | 500 | gb\|AAL26896.1\|AF317621_1 cadherin-related midgut membrane protein [L. dispar] |
| Locus 4003 | 501 | ref\|NP_001129360.1\|osiris 9 [Bombyx mori] |
| Locus 5421 | 450 | ref\|NP_001129360.1\|osiris 9 [B. mori] |
| Locus 1129 | 500 | ref\|NP_001129361.1\|osiris 18 [B. mori] |
| Locus 4413 | 450 | ref\|XP_001623928.1\|predicted protein [Nematostella vectensis], \|gb\|ABS88989.1\| vitellogenin [Rhipicephalus microplus] |
| Locus 365 | 208 | Locus_365_Transcript [L. dispar] |
| Locus 27440 | 500 | ref\|XP_002096601.1\|GE25755 [Drosophila yakuba] |
| Locus 28365 | 250 | Locus_28365_Transcript [L. dispar] |

Target sequences were amplified from L. dispar genomic DNA. The resulting PCR products were further amplified using primers flanked with T7 RNA polymerase promoter sequences for synthetic dsRNA analysis experiments. T7-promoter-containing sequences were PCR amplified DNA and transcribed to dsRNA using T7 RNA polymerase utilizing linked T7 promoters. Sense strand dsRNA sequences without the T7 sequences (SEQ ID NOs. 1-5), the L4440 sequence used as an "empty vector sequence" control (SEQ ID NO. 6), and the LacZ sequence used as "mock RNAi" control (SEQ ID NO. 7) are listed in Table 2.

TABLE 2 dsRNA species for L. dispar RNAi analysis

| Source | Sense Strand Sequence |
|---|---|
| Locus 22 | ATGCATATGCGTGCAAGGTTTCCTTAATCAGCCGGCAGCCACGACAAGTCCC<br>GTAACCACCAGAAACACAATATTTGCTGATGAAAAATTTGAAGGTGAAATC<br>TTCGAAGATCTCGATGTATTTGAACAATTAGACATAACTGCAAGAAACAGTG<br>AACTCTACAGATTACCGAACACCACAAAACCGAGTCACTATACCGTCTTGTG<br>GACGCTGGACTTCTCACGAGCAATTCCAACACAATCTGGCACGGTTTCAATA<br>TTGCTAAATGCTACTCAGGCTAATGTTAATGAAATAGTAATCCACGCTCACA<br>ATCTAACCATTACCAATGTAAGACTACAGTTAGGTACTACAGAAGTCCCAGT<br>CACCTATACTTTAGAACCAGAATATCATTTCATGAGAATTCGATTAAACGAA<br>GGTTCGTTGAACTATAATCCCACAACTCCTAATACTATACTCTCACAATCG<br>ATTTTGGTGCCAATCTGCGTGATGACATGTACG (SEQ ID NO. 1) |

TABLE 2 -continued dsRNA species for *L. dispar* RNAi analysis

| Source | Sense Strand Sequence |
|---|---|
| Locus 365 | TTTTTGGAAGTAAAACCACGATTTAAACAACAGAGGTACAGGATGGATGAA<br>ATTATTGAAATAGAACTATATGTGAGATTGTCATACAACACAGTTCTTGAAG<br>TAAAGAAATGCTCTGTAGCTATATCTGGTCACACTGAAACTATTGAAATATC<br>AATAACTGATAATGACAATACTGTTATATCTTTGGAAGGTGGTAGAGTTAAG<br>A (SEQ ID NO. 2) |
| Locus 28365 | TTTACATAAATACAGCCACATTGGTTGGACCATATTTTCTACCATATCAATA<br>AAGCTTATACAAAAATCTAAGTTTATACAAAATCATTTTCTACTAATTTACA<br>AGGACACATATGAAACTACTACGCTGGTAGCAATTTCAGACATGTGGTCACA<br>CTGAAAAAGCTGCAAGCTTTAAAAGGATCACCATTAGCTTTAAACAACGTTA<br>TGTCATATTTTAATAAAATGCGATTCTTAATGCAAATCTGCT<br>(SEQ ID NO. 3) |
| Locus 5421 | TGGATCTGCAAGATCAGCTCGTAGCTATGAACCTTTAGCCAATGATCCTCAG<br>ACGAGAGAACTTCAGATTAACGAAAGAATAGCTGATAACGTTGGCGACTTC<br>TTAGACAATCACGTACTGCAATTGCGTCTAACCGAACCTGATGGTGAATCCC<br>GATCTCTTGATGAGGAAGCTCGTGGCAAGAAGATCAAGAAGAAGAAGCTCA<br>AGAAGCTGTTGCCCCTCCTTCTCCTTTTGAAGCTGAAATTCGCTGCCCTCATT<br>CCACTTTTCCTTGGTATCATCGCAATCGTTGCCGTTAAAGCCGTCTTCCTTGG<br>AAAGATTGCATTCGCCATGAATGCAATCAGCTTGATAAGAAAACTTATGGCA<br>AAGAAGAATGGAGGAGGTTCCTCATCGAGCATTTCCTGGGCTGCTCCTCAAC<br>ATACGGATGAGCATCCAGGATATTCTTATGAACCCGCTCAGTCTCAAGGATG<br>GGGTCGGCAGGCCAGTGATGGCGCGGACTTAG (SEQ ID NO. 4) |
| Locus 4413 | CACGCCTTGGAATCGTATAAACTATTCTAGAAGTAGCCAGTATAAGTGGTAGC<br>AACATTCTCCTGAAATGTTTGTATCAATAACTGCGATAACCAACTAGCTGCTCA<br>AGCTTAACCCTGGATAGTCTATTTAACTGAAAGTCTACTCTGAAGGCTGACGCT<br>CTAGTTATATCTCACAGACGACGAGTGTCGTTGATGTTAGGTGCGCTAATTTAT<br>ACTAAGCACCGACATCGCTCCAAATATCCCTTCAGTAGTTCTGCGTGACGATCC<br>TAGACGTTATGGTAGTGACGTCATTGTTTTCTCTCACGGCACACTCACAACGAC<br>CCTATACACAAACGCATACTGATTAGACATGCTGTGCATTTGAAGTTTCAGATC<br>TGGATACTAGAATAACATTACACCGGTTTCGTATACTATAGTGAATACGAAATT<br>ATTTCAGAATATCCGAGTTTCGAATTATCCAACAGTTTCGGATTATCCTACGAT<br>TACGGGTTATCCGAC (SEQ ID NO. 5) |
| L4440 | TAATACGACTCACTATAGGGAGACCGGCAGATCTGATATCATCGATGAATTC<br>GAGCTCCACCGCGGTGGCGGCCGCTCTAGAACTAGTGGATCCACCGGTTCCA<br>TGGCTAGCCACGTGACGCGTGGATCCCCCGGGCTGCAGGAATTCGATATCAA<br>GCTTATCGATACCGTCGACCTCGAGGGGGGGCCCGGTACCCAATTCGCCCTA<br>TAGTGAGTCGTATTA (SEQ ID NO. 6) |
| LacZ | TGAAAGCTGGCTACAGGAAGGCCAGACGCGAATTATTTTTGATGGCGTTAAC<br>TCGGCGTTTCATCTGTGGTGCAACGGGCGCTGGGTCGGTTACGGCCAGGACA<br>GTCGTTTGCCGTCTGAATTTGACCTGAGCGCATTTTTACGCGCCGGAGAAAA<br>CCGCCTCGCGGTGATGGTGCTGCGCTGGAGTGACGGCAGTTATCTGGAAGAT<br>CAGGATATGTGGCGGATGAGCGGCATTTTCCGTGACGTCTCGTTGCTGCATA<br>AACCGACTACACAAATCAGCGATTTCCATGTTGCCACTCGCTTTAATGATGA<br>TTTCAGCCGCGCTGTACTGGAGGCTGAAGTTCAGATGTGCGGCGAGTTGCGT<br>GACTACCTACGGGTAACAGTTTCTTTATGGCAGGGTGAAACGCAGGTCGCCA<br>GCGGCACCGCGCCTTTCGGCGGTGAAATTATCGATGAGCGTGGTGGTTATGC<br>CGATCGCGTCACACTACGTCTGAACGTCGAAAACCCGAAACTGTGGAGCGC<br>CGAAATCCCGAATCTCTATCGTGCGGTGGTTGAACTGCACACCGCCGACGGC<br>ACGCTGATTGAAGCAGAAGCCTGC (SEQ ID NO. 7) |

Cloning and dsRNA Expression in *E. coli* HT115(DE3)

Genes specific to *L. dispar* were selected by examining *L. dispar* transcriptomic profiles (Sparks & Gundersen-Rindal, Viruses, (2011) 3:12, 2339-50; Sparks et al., PloS One, (2013) 8:5, e61190), and regions of interest for each gene selected that varied between 200 to 500 base pairs. PCR products were then generated by polymerase chain reaction (PCR) by amplifying genomic DNA using oligonucleotides listed in Table 3

TABLE 3

PCR Primers for *L. dispar* target genes.

| Gene | Direction | Sequence (5'-3') |
|---|---|---|
| Locus 22 (Aminopeptidase N1) | Forward | ATGCATATGCGTGCAAGGT (SEQ ID NO. 8) |
| Locus 22 (Aminopeptidase N1) | Reverse | CGTACATGTCATCACGCAG A (SEQ ID NO. 9) |

TABLE 3 -continued

PCR Primers for *L. dispar* target genes.

| Gene | Direction | Sequence (5'-3') |
|---|---|---|
| Locus 365 | Forward | TTTTTGGAAGTAAAACCACGA (SEQ ID NO. 10) |
| Locus 365 | Reverse | TCTTAACTCTACCACCTTCCAAAGA (SEQ ID NO. 11) |
| Locus 28365 | Forward | TTTACATAAATACAGCCACATTGGT (SEQ ID NO. 12) |
| Locus 28365 | Reverse | AGCAGATTTGCATTAAGAATCG (SEQ ID NO. 13) |
| Locus 5421 (Osiris 9) | Forward | TGGATCTGCAAGATCAGCTC (SEQ ID NO. 14) |
| Locus 5421 (Osiris 9) | Reverse | CTAAGTCCGCGCCATCACT (SEQ ID NO. 15) |
| Locus 4413 (Vitellogenin) | Forward | CACGCCTTGGAATCGTATAAA (SEQ ID NO. 16) |
| Locus 4413 (Vitellogenin) | Reverse | GTCGGATAACCCGTAATCGT (SEQ ID NO. 17) |

PCR-amplified DNA was precipitated using 3M sodium acetate and 100% ethanol to be purified by agarose gel electrophoresis. The resulting fragments were cloned into the multiple cloning site (MCS) of L4440 plasmid (Addgene plasmid 1654) (Timmons et al., Gene, (2001) 263:1-2, 103-12) using SmaI and PmlI restriction sites to give L4440-Locus 22, L4440-Locus 365, L4440-Locus 28365, L4440-Locus 5421 and L4440-Locus 4413 constructs. Subsequently each plasmid was transformed using standard $CaCl_2$ transformation protocols into the RNase III deficient *E. coli* strain HT115(DE3) obtained from *Caenorhabditis* Genetics Center (CGC) at the University of Minnesota (Timmons et al., Gene, (2001) 263:1-2, 103-12) and plated on ampicillin and tetracyclin containing NZCYM-agar plates.

An overnight culture of 100 ml NZCYM containing appropriate antibiotics was inoculated with a single colony of the above transformed HT115(DE3)+plasmid and grown at 37° C. This overnight culture was used to inoculate a 500 ml NZCYM media to an $OD_{600}$=0.05 and grown to an $OD_{600}$=0.4. The cells were induced by the addition of Isopropyl-b-d-thiogalactopyranoside (IPTG) to a final concentration of 0.4 mM and allowed to grow for 4 h at 37° C. The cells were harvested by centrifugation in a Sorvall rotor at 5000 rpm for 15 min, weighed and stored at −80° C. until used.

To confirm the synthesis of dsRNA in bacteria, a part of the culture was analyzed to confirm dsRNA expression of the selected fragments (FIG. 1). The observed bands were insensitive to RNase A and DNase treatments and hence were assumed to be dsRNA. The differences in size between the cloned fragments and the induced dsRNA were due to the gene portion in the L4440 vector. This contributed to approximately 163 bp that is evident from the mobility of the dsRNA bands (FIG. 1, lanes 3, 4, 6, 7 and 8). To avoid any phenotypes that may have resulted due to the L4440 plasmid vector, we used the empty vector as a control to monitor its effect on the larvae (FIG. 1, lane 2).

In Vitro Synthesis of Double Stranded RNA:

RNAi synthesis was performed in the gut tissue of *L. dispar* larvae. The PCR products described above were used to generate dsRNA required for RNAi in the gut tissue of *L. dispar* and *M. sexta*. The primers used for PCR contained the T7 promoter sequence (5'-GAATTAATACGACTCACTATAGGGAGA-3'). LacZ, a gene that encodes ß-galactosidase was amplified from the *E. coli* genomic DNA and served as a negative control (mock) for RNAi experiments (all primers used are listed in Table 4). The PCR-amplified DNA was purified using a PCR purification kit (Qiagen). In vitro transcription to yield dsRNA was performed either by using MEGASCRIPT RNAi kit (Life Technologies) or by combining 1× buffer (Promega); containing 40 mM Tris (pH 7.9), 6 mM MgCl2, 2 mM spermidine and 10 mM NaCl, 1 units of SUPERase® In RNase inhibitor (Life Technologies), 10 mM Dithiothreitol (DTT), 7.5 mM each rNTP, and 2.5 µg PCR amplified DNA in a final volume of 40 µl were incubated at 37° C. for 5 min. After 5 min, 40 units of T7 RNA polymerase (Promega) was added to the reaction and further incubated at 37° C. overnight.

TABLE 4

PCR Primers for *L. dispar* target genes in vitro dsRNA production.

| Gene | Direction | Sequence (5'-3') |
|---|---|---|
| Locus 22 (Aminopeptidase N1) | Forward | GAATTAATACGACTCACTATAGGGAGAATGCATATGCGTGCAAGGT (SEQ ID NO. 18) |
| Locus 22 (Aminopeptidase N1) | Reverse | GAATTAATACGACTCACTATAGGGAGACGTACATGTCATCACGCAGA (SEQ ID NO. 19) |
| Locus 365 | Forward | GAATTAATACGACTCACTATAGGGAGATTTTGGAAGTAAAACCACGA (SEQ ID NO. 20) |
| Locus 365 | Reverse | GAATTAATACGACTCACTATAGGGAGATCTTAACTCTACCACCTTCCAAAGA (SEQ ID NO. 21) |
| Locus 28365 | Forward | GAATTAATACGACTCACTATAGGGAGATTTACATAAATACAGCCACATTGGT (SEQ ID NO. 22) |
| Locus 28365 | Reverse | GAATTAATACGACTCACTATAGGGAGAAGCAGATTTGCATTAAGAATCG (SEQ ID NO. 23) |
| Locus 5421 (Osiris 9) | Forward | GAATTAATACGACTCACTATAGGGAGATGGATCTGCAAGATCAGCTC (SEQ ID NO. 24) |
| Locus 5421 (Osiris 9) | Reverse | GAATTAATACGACTCACTATAGGGAGACTAAGTCCGCGCCATCACT (SEQ ID NO. 25) |
| Locus 4413 (Vitellogenin) | Forward | GAATTAATACGACTCACTATAGGGAGACACGCCTTGGAATCGTATAAA (SEQ ID NO. 26) |
| Locus 4413 (Vitellogenin) | Reverse | GAATTAATACGACTCACTATAGGGAGAGTCGGATAACCCGTAATCGT (SEQ ID NO. 27) |
| LacZ | Forward | GAATTAATACGACTCACTATAGGGAGATGAAAGCTGGCTACAGGA (SEQ ID NO. 28) |
| LacZ | Reverse | GAATTAATACGACTCACTATAGGGAGAGCAGGCTTCTGCTTCAAT (SEQ ID NO. 29) |

The reactions were then centrifuged for 2 min at 13,000 rpm to pellet the magnesium pyrophosphate. The supernatant was transferred was treated with 2 units of RQ1 DNase followed by incubation at 37° C. for 30 min. The reaction mixture was extracted with an equal volume of phenol/chloroform/isoamyl alcohol (25:24:1) and centrifuged. The aqueous layer was extracted with chloroform. To the resulting aqueous layer, one-fifth-volume ammonium acetate (5 M ammonium acetate+100 mM EDTA) and 3 volumes of chilled 100% ethanol was added. After incubating on ice for 10 min, the dsRNA was precipitated, washed with 75% ethanol and dissolved in nuclease free water.

RNAi in *L. dispar*:

Two approaches were used in dsRNA feeding to investigate the effect of ingested RNAi in *L. dispar* and *M. sexta*. dsRNAs were either (1) expressed in the bacteria HT115 (DE3) or (2) synthesized by in vitro transcription, as described above. Both were then mixed with the appropriate artificial diets and then fed to the respective insects.

For feeding either bacterially-expressed or in vitro synthesized dsRNA, a freeze-dried artificial diet pellet was powdered and placed in the well of a plastic bioassay tray (Bio-BA 128; BioServ, Frenchtown, N.J.). The diet was rehydrated by applying 300 μl of dsRNA induced bacterial culture and green food coloring to monitor dietary intake (Martin, Biol Control, (2004) 29:1, 109-14). To test for in vitro synthesized dsRNA, 24 mg of the freeze-dried artificial diet was rehydrated using 20 μg of dsRNA in a total volume of 100 μl and 2% PEG 8000. Larvae, which entered the third instar and were starved for 24 h, were placed on each pellet. A total of 3 larvae per individual target gene were so treated. A positive control consisting of either the empty vector alone or mock control consisting of LacZ dsRNA as well as a negative control of water only were also tested. Larvae were placed at 27° C. and observed until they reached the adult stage (if they survived). During this period the total body mass and the egg masses of the females reaching the adult stage were monitored for the long-term effects of RNAi.

Figure 2A:
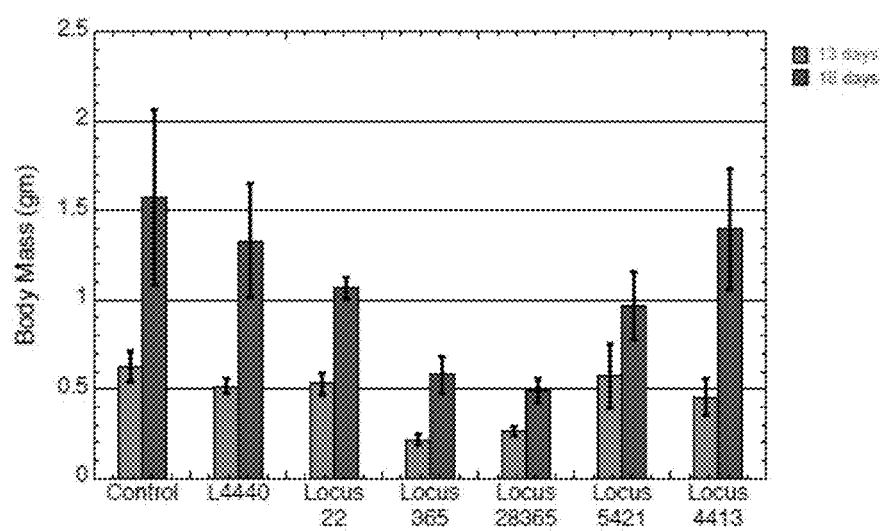
FIGS. 2A and 2B provide analysis of bacterial-induced RNAi in L. dispar larvae.

RNAi has been previously demonstrated to be effective when animals were allowed to feed continuously on extracelluar dsRNA (Timmons et al., Gene, (2001) 263:1-2, 103-112; Li et al., PloS One, (2011) 6:3, e17788). In order to study the effects of RNAi, bacteria suspensions containing induced dsRNA were mixed with an artificial diet and fed continuously to *L. dispar* third instar larvae for 5 contiguous days. To investigate the long-term effect of dsRNA feeding, the larvae were then transferred to artificial diet devoid of dsRNA (referred to as "AD"). The body masses of these larvae were assessed over a period of 3 weeks. Observations indicated that the larvae fed with either "locus 365" (SEQ ID NO. 2) and "locus 28365" dsRNA (SEQ ID NO. 3) showed a striking two-fold loss in body mass after 13 and 18 days post-feeding of dsRNA (FIG. 2A).

Seeking a sustainable method for delivery of the dsRNA products disclosed herein for biocontrol of pests, we examined the possibility of feeding synthetic dsRNA to *L. dispar* targets. Using Bt as pesticide is a common practice, but using bacterial culture as a large-scale delivery system is less feasible. Moreover a previous study reported gene silencing induced by L4440 empty vector that was used as a control (Grishok et al., Genes & Develop, (2005) 19:6, 683-96) although we did not observe such an occurrence. To examine the possibility of using in vitro created dsRNA as biocontrol agents, T7 flanked DNA fragments of Loci 22, 365, 28365, 5421 and 4413 (FIG. 3 A, lanes 2-6) were transcribed in vitro to generate the respective dsRNA (FIG. 3B, lanes 2-6). The transcribed dsRNA was evaluated alongside a DNA marker and slower mobility was observed which is common when comparing dsRNA to dsDNA (Livshits et al., J. Biomol Struct Dynam, (1990) 7:6, 1237-49). LacZ dsRNA (SEQ ID NO 12) was also synthesized and used as a control (FIG. 3C). The dsRNA species were observed to be stable over the period of feeding (data not shown).

To study the effect of RNAi on the level of transcripts, the larvae were fed on synthetic dsRNA continuously for 5 days. The diets were replenished again after 3 days of feeding. For insects fed dsRNA-containing bacterial strains, the insects were fed until the supplemented diet was consumed completely, usually within 48-72 hours. A similar condition of feeding was conducted with *M. sexta* larvae.

Figure 4A:
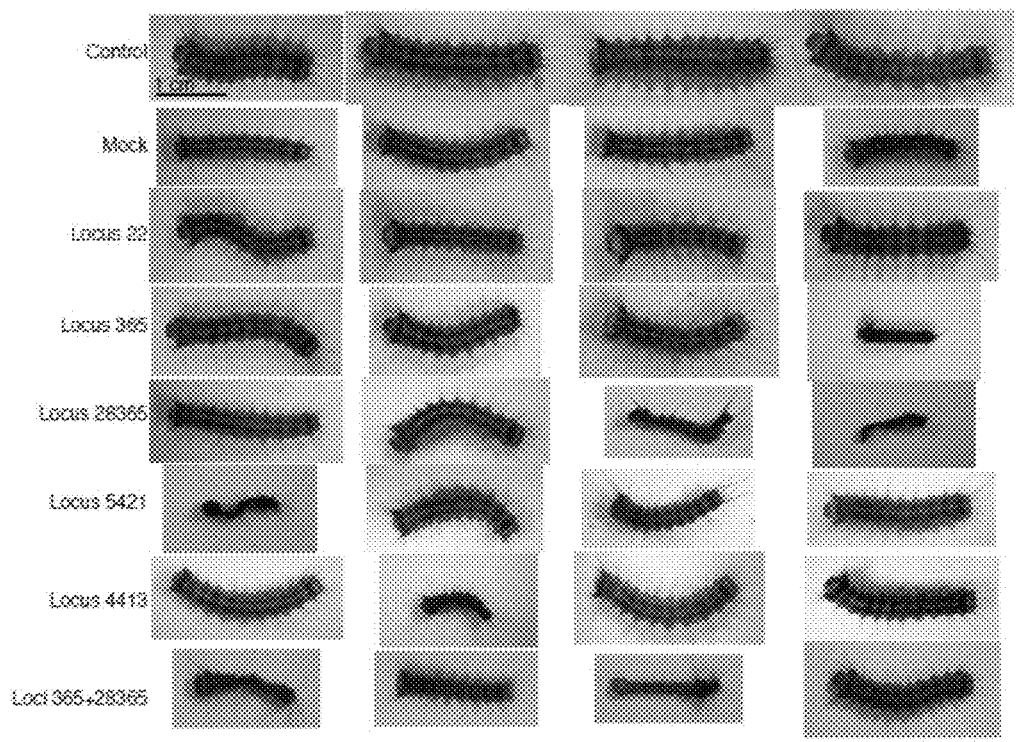
FIGS. 4A and 4B provide analysis of the effects of RNAi on L. dispar larvae. Third instar larvae were fed on in vitro transcribed dsRNA indicated here as LacZ RNAi (Mock), Locus 22, Locus 365, Locus 28365, Locus 5421, Locus 4413 or a combination of Locus 365 and Locus 28365 for a period of 5 days following which the larvae were moved to artificial diet. As a negative control artificial diet was mixed with water prior to feeding larvae (control).

The effect of long-term RNAi was investigated in *L. dispar* by allowing the larvae to feed on in vitro synthesized dsRNA for 5 days and subsequently moving them to AD. Developmental and other phenotypic effects were analyzed. Control larvae (fed only on water and diet without any dsRNA) were better developed in terms of body mass as compared to the mock control fed on lacZ dsRNA (FIG. 4A, compare panels a1-a4 to b1-b4). However, all the control- and mock-treated larvae developed into healthy adults. The larvae fed in vitro transcribed dsRNA showed inhibited development and higher mortality as compared to control- and mock-treated animals.

Larvae treated with RNAi against locus 28365 (FIG. 4A, panel e4; SEQ ID NO. 3) and locus 5421 (FIG. 4A, panel f1, SEQ ID NO. 4) deceased 2 days after stopping per os dsRNA treatment. More mortality was recorded in larvae treated with dsRNA for locus 365 (FIG. 4A, panel d4; SEQ ID NO. 2), locus 28365 (FIG. 4A, panel e3; SEQ ID NO. 3), locus 4413 (FIG. 4A, panel g2; SEQ ID NO. 5) and loci 365+28365 (FIG. 4A, panels h1 & h3; SEQ ID NO. 2 and SEQ ID NO. 3, respectively) after 4 days of stopping dsRNA feeding. We also observed the locus 5421 (FIG. 4A, panel f4; SEQ ID NO. 4) and loci 365+28365 (FIG. 4A, panel h2; SEQ ID NO. 2 and SEQ ID NO. 3, respectively) were deceased by 10 days of stopping per os feeding of dsRNA. Next we measured the egg mass from newly emerged adults as a measure of fecundity. Females were observed only in the control (FIG. 4A, panels a1, a3 & a4), mock (FIG. 4A, panel b1; SEQ ID NO. 12) and locus 365 (FIG. 4A, panels d1 & d2; SEQ ID NO. 2) animals. After comparing the egg masses in these females, we found that females receiving "locus 365" dsRNA (SEQ ID NO. 2) produced half as many eggs compared to the control or mock-treated animals (data not shown). None of the other dsRNA species targeting the other loci produced any noticeable effect on egg production.

In a separate experiment, egg mass was measured directly. Insects fed dsRNA for locus 365 (SEQ ID NO. 2) showed a 1.6-fold lower egg mass compared to the control. Insects fed dsRNA for locus 28365 (SEQ ID NO. 3) showed a 1.7-fold lower egg mass compared to the control. When the dsRNA for loci 365+28365 (SEQ ID NO. 2 and SEQ ID NO. 3, respectively) were fed in combination to *L. dispar* larvae, the resulting egg mass produced was 2.37-fold lower than the control.

Figure 4B:
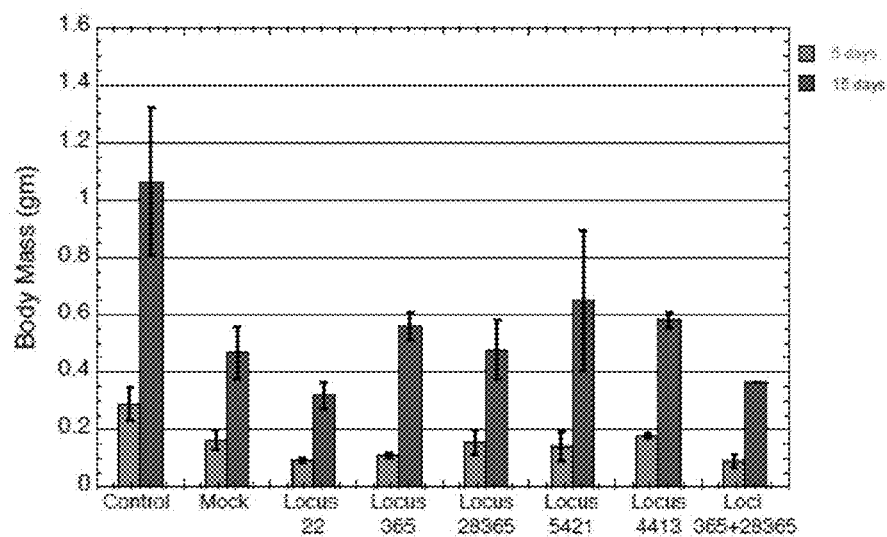

Body mass of treated larvae at fifth- and fifteenth-day stages post dsRNA treatment was also analyzed. A two-fold lower body mass in larvae for those receiving dsRNA for locus 22 (SEQ ID NO. 1), locus 365 (SEQ ID NO. 2) and loci 365+28365 (SEQ ID NO. 2 and SEQ ID NO. 3, respectively) compared to mock treated and approximately 3-fold change when compare to the control at fifth day stage (FIG. 4B). Although after 15 days of rearing these larvae post dsRNA feeding, there were only very minor difference in the body masses of the dsRNA treated larvae compared to the mock treated ones, a significant difference was observed when compared to the control (FIG. 4B). No significant differences were noted at either time for the other loci tested. These results together indicated that the RNAi targeted to deplete expression of proteins encoded by the locus 22, locus 365, and the combination of loci 365+28365 genes affected both development and fecundity of the animals.

Figure 2B:
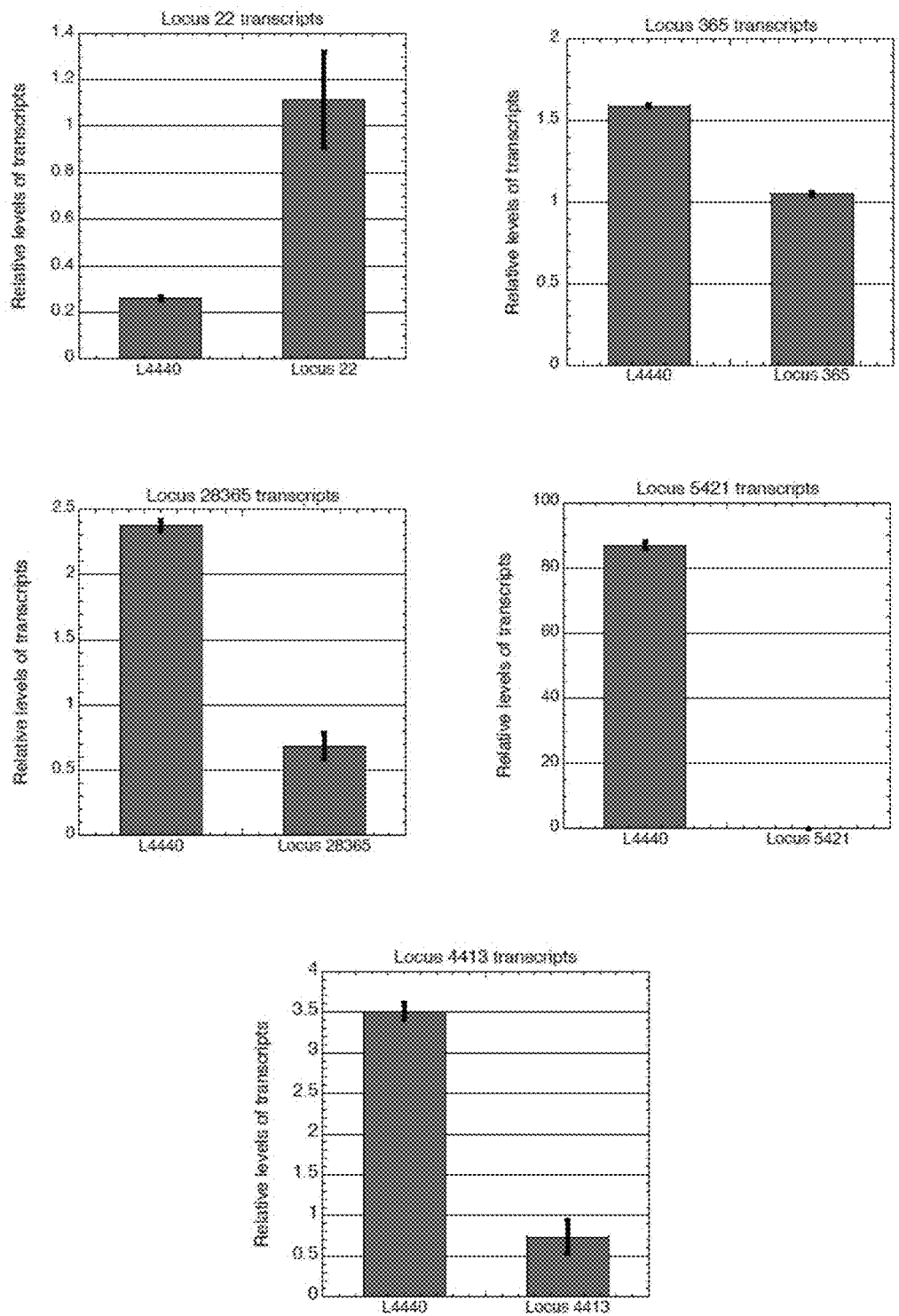
Figure 5:
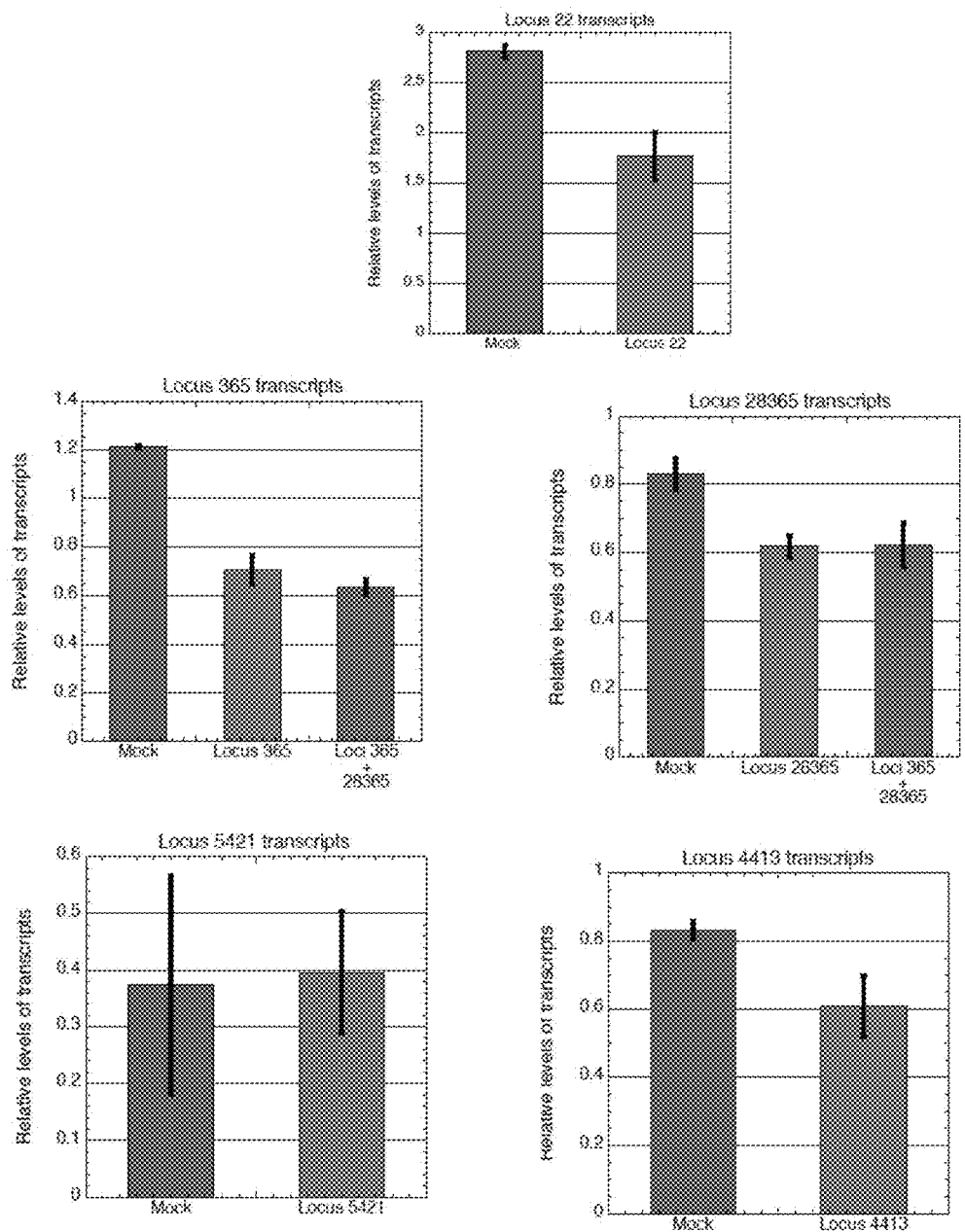
FIG. 5 provides analysis of quantitative RT-PCR analysis of transcript levels after RNAi mediated depletion of genes in *L. dispar*. Total RNA from gut tissue of *L. dispar* larvae fed on dsRNA; Locus 22, Locus 365, Locus 28365, Locus 5421, Locus 4413 or a combination of Locus 365 and Locus 28365 was isolated and the levels of transcripts were measured by qPCR. LacZ RNAi (Mock) served as a negative control. 18 s RNA was used as an internal standard to correct for differences in RNA recovery from tissues, Results are from three biological replicates, and error bars indicate SEM.

The results revealed that gypsy moth larvae could orally ingest either bacterial induced or in vitro synthesized dsRNA for depletion of midgut genes (FIGS. 2B & 5). Insects treated with dsRNA specific for locus 365 (SEQ ID NO. 2) and locus 28365 (SEQ ID NO. 3) showed a consistent depletion of the target genes. Additionally, when these two dsRNA species were ingested in combination, test insects displayed an additive effect, suggesting a synergistic effect. The phenotypic analysis of larvae fed this combination of dsRNA products demonstrated poor development and higher mortality attributed to depletion of translation of the target genes (FIG. 4A).

Delivering dsRNA per os has several advantages over other labor-intensive techniques such as microinjection, and also allows for delivery of dsRNA in a large scale. However, we also analyzed a transfection approach. Transfection reagents were evaluated for their efficiency in dsRNA uptake in UGA-CiE1 cell line from *Chrysodeixis includens* (Lepidoptera: Noctuidae) and *D. melanogaster* embryos with varying results (Johnson et al., Insect Biochem Mol Biol, (2010) 40:5, 394-404; Whyard et al., Insect Biochem Mol Biol, (2009) 39:11, 824-32). We did not observe RNAi in IPLB-LdEp gypsy moth tissue culture cells upon transfection of in vitro synthesized dsRNA using lipofectamine 3000 (data not shown).

Quantitative Real-Time PCR Analysis

If RNAi induced physiological variations in the treated animal, then depletion of the mRNAs transcribed by the target genes upon dsRNA ingestion should be observed in insects treated with both bacterially produced and in vitro produced dsRNA. To test this prediction, we continuously fed synthetic dsRNA with artificial diet to the third instar larvae for a period of 5 days. The levels of each transcript were assayed by qPCR for three biological replicates.

Transcript expression levels were measured by quantitative realtime PCR (qPCR) using SYBR green PCR master mix from Applied Biosystems or SensiMix SYBR from Bioline. The reactions were performed on an Applied Biosystems 7500 real-time PCR system. Data were analyzed with ABI Prism sequence detection system software. All analysis was performed in the linear range of amplification. Standards were determined by serial dilution of the cDNA prepared from total RNA isolated from gut tissue of a normal animal and used as a reference standard for the quantification of cDNA produced from RNA. 18s RNA was used as an internal standard to correct for differences in RNA recovery from tissues (Sparks et al., 2013, *PloS one*, (2013) 8:5, e61190).

Total RNA was isolated from the tissue samples by either soaking in 1 ml volume of TRIzol (Invitrogen) or by using the RNeasy kit (Qiagen). Reverse transcriptase PCR was used to generate cDNA, 200 ng of total RNA was incubated with a 0.5 mM deoxynucleoside triphosphate mixture, 0.65 µM each oligo(dT)$_{16}$ (Life Technologies), and random hexamers (Life Technologies) at 65° C. for 5 min. A cDNA synthesis mixture containing 10 mM dithiothreitol (DTT), 100 units of SUPERSCRIPT Reverse Transcriptase III (Life Technologies), and 2 units of SUPERase In RNase inhibitor (Life Technologies) was then added to the total RNA mixture, which was incubated at 25° C. for 5 min, 50° C. for 50 min. The reaction was terminated by incubation at 70° C. for 15 min. The resulting cDNA was then evaluated with primers listed in Table 5 for specific genes by qPCR.

TABLE 5 qPCR Primers.

| Gene | Direction | Sequence (5'-3') |
|---|---|---|
| Locus 22 (Aminopeptidase N1) | Forward | CAACTCCTCAATACTATA CTCTCACAATCG (SEQ ID NO. 30) |
| Locus 22 (Aminopeptidase N1) | Reverse | TCAGTAGGATTGTTCCTG AACCAA (SEQ ID NO. 31) |
| Locus 365 | Forward | CTCTGTAGCTATATCTGG TCACACTGAA (SEQ ID NO. 32) |
| Locus 365 | Reverse | TCTCTTAACTCTACCACC TTCCAAAGA (SEQ ID NO. 33) |
| Locus 28365 | Forward | AGCCACATTGGTTGGACC AT (SEQ ID NO. 34) |
| Locus 28365 | Reverse | GCGTAGTAGTTTCATATG TGTCCTTGTA (SEQ ID NO. 35) |
| Locus 5421 (Osiris 9) | Forward | TCCTGAAGGACTTGGATA TCTTTGA (SEQ ID NO. 36) |
| Locus 5421 (Osiris 9) | Reverse | GTCTGAGGATCATTGGCT AAAGGT (SEQ ID NO. 37) |
| Locus 4413 (Vitellogenin) | Forward | CGAAAAAATCCACCATTA CTTTCA (SEQ ID NO. 38) |
| Locus 4413 (Vitellogenin) | Reverse | TTCAGGAGAATGTTGCTA CCACTT (SEQ ID NO. 39) |
| L. dispar 18S | Forward | GTCTCGCAGCCGTATTAA GGCGA (SEQ ID NO. 40) |
| L. dispar 18S | Reverse | GCACTCATCCCATCACTG GTCAGA (SEQ ID NO. 41) |
| M. sexta 18S | Forward | CCGGTAACGAACGAGACT CTA (SEQ ID NO. 42) |
| M. sexta 18S | Reverse | GGGCATCACAGACCTGTT ATT (SEQ ID NO. 43) |

The levels of target transcripts were evaluated by qPCR in the gut of a subset of the larvae following ingestion of bacterially expressed dsRNA. The expression of loci 365, 28365, 5421 and 4413 (SEQ ID NOs. 2, 3, 4, and 5, respectively) were significantly reduced (FIG. 2B). Unexpectedly, locus 22 (SEQ ID NO. 1) showed a marked 5-fold increase in the level of transcript (FIG. 2B). This may have been a result of an undetermined dose response, but was not observed in subsequent experimentation. These results demonstrated that RNAi may be achieved by feeding bacterial induced dsRNA to *L. dispar* larvae.

To test if the two loci 365 (SEQ ID NO. 2) and 28365 (SEQ ID NO. 3) had any potential additive or synergistic effects, we combined these dsRNA in the diet. Observations revealed that RNAi against loci 22 (SEQ ID NO. 1), 365 (SEQ ID NO. 2), 28365 (SEQ ID NO. 3), and 4413 (SEQ ID NO. 5) significantly depleted the level of expression of these transcripts (FIG. 5). We did not note hyper-expression of locus 22 (SEQ ID NO. 1) as observed earlier, but there was no significant depletion in expression of locus 5421 (FIG. 2; (SEQ ID NO. 4)). There were variations in the depletion of certain loci although we have continually observed depletion in the expression of loci 365, 28365 and 4413 (FIGS. 2 & 5). The results indicate that RNAi in L. dispar can be successfully accomplished by feeding L. dispar larvae in vitro synthesized dsRNA.

Synthesis of cDNA for Transcript Level Measurements

To measure the level of gene expression the gut tissue of either L. dispar or M. sexta was isolated by dissection subsequent to dsRNA treatment. Total RNA was isolated from the tissue samples by either soaking in 1 ml volume of TRIzol (Invitrogen) or by using the RNeasy kit (Qiagen). Reverse transcriptase PCR was used to generate cDNA, 200 ng of total RNA was incubated with a 0.5 mM deoxynucleoside triphosphate mixture, 0.65 µM each oligo(dT)$_{16}$ (Life Technologies), and random hexamers (Life Technologies) at 65° C. for 5 min. A cDNA synthesis mixture containing 10 mM dithiothreitol (DTT), 100 units of SUPERSCRIPT Reverse Transcriptase III (Life Technologies), and 2 units of SUPERase In RNase inhibitor (Life Technologies) was then added to the total RNA mixture, which was incubated at 25° C. for 5 min, 50° C. for 50 min. The reaction was terminated by incubation at 70° C. for 15 min. The resulting cDNA was then evaluated with primers listed in Table 5 for specific genes by qPCR.

dsRNA Specificity for L. dispar.

Figure 6:
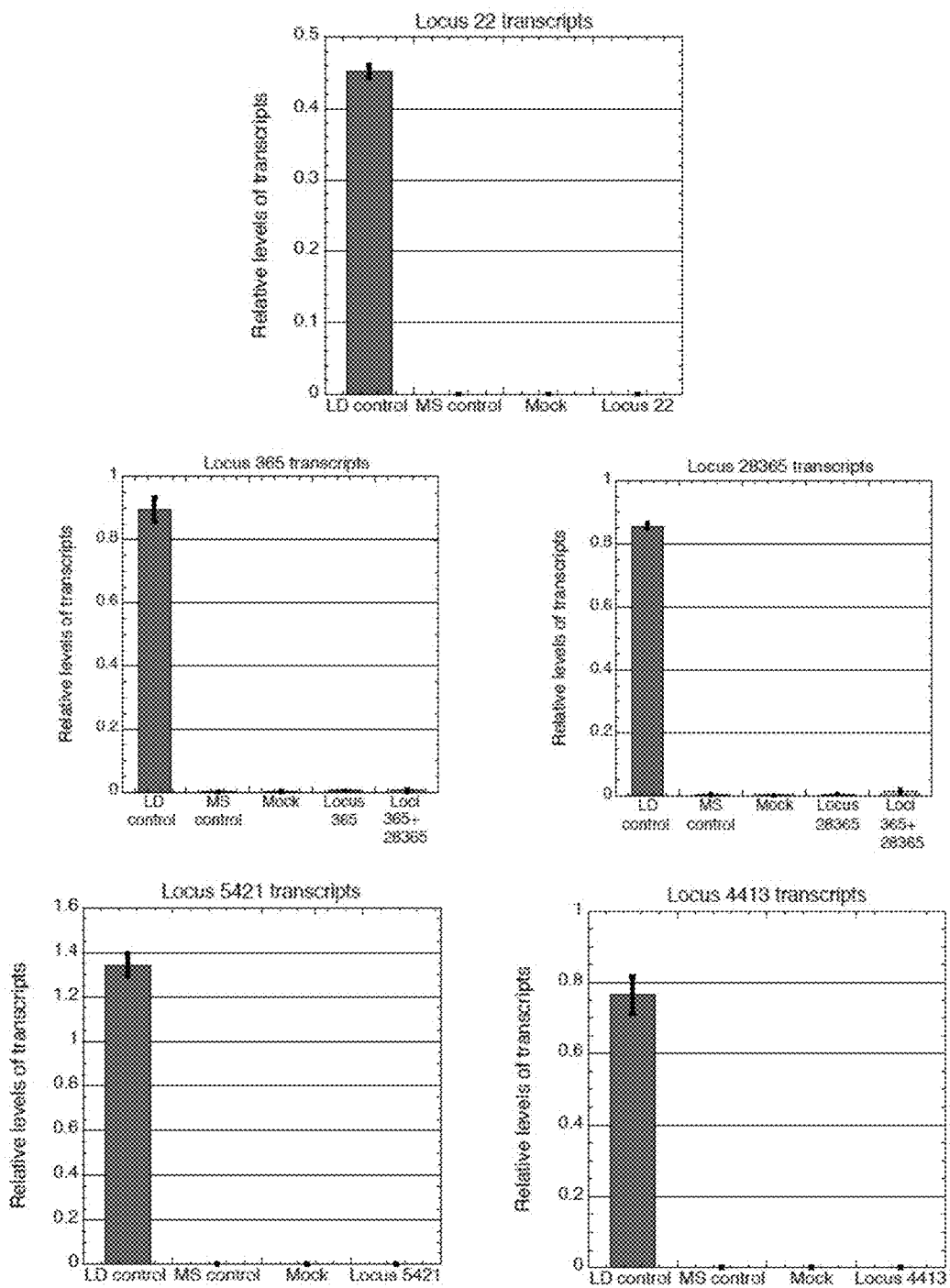
FIG. 6 provides a comparative analysis for RNAi specificity of *L. dispar* genes in *Manduca sexta*. Total RNA from gut tissue of *M. sexta* larvae fed on *L. dispar* specific dsRNA (Locus 22, Locus 365, Locus 28365, Locus 5421, Locus 4413 or a combination of Locus 365 and Locus 28365) was isolated and the levels of transcripts were measured by qPCR. LacZ RNAi (Mock) served as a negative control. Expression of the above transcripts were compared to *L. dispar* and indicated in each graph. 18s RNA respective to each animal was used as an internal standard to correct for differences in RNA recovery from tissues. Results are from three biological replicates, and error bars indicate SEM.

Specificity of L. dispar dsRNA in M. sexta. One of the advantages of using RNAi as a pest control agent is the specificity of the dsRNA for a particular target. To determine whether the dsRNA species described herein showed specificity to L. dispar, the dsRNA species were fed to Manduca sexta larvae and the effect on expression of the target genes. Protocols used were similar to those described above. After ingestion of dsRNA, the expression of these genes in the gut were analyzed by qPCR and were compared to the L. dispar. Interestingly we observed that neither of the loci was expressed in M. sexta controls (FIG. 6). Accordingly, we infer that the genes were specific to L. dispar when compared to M. sexta. This is an important observation for the development for insect specific targets for biocontrol of pests.

What is claimed is:

1. A double-stranded ribonucleic acid (dsRNA) comprising a sense region with at least 99% or 100% sequence identity to SEQ ID NO: 2, and an antisense region comprising a second sequence complementary to the sense region.

2. The dsRNA of claim 1, wherein the sense region consists of SEQ ID NO: 2.

3. The dsRNA of claim 1, wherein the dsRNA is expressed in a plant cell.

4. The dsRNA of claim 3, wherein the plant cell is a hardwood tree cell.

5. The dsRNA of claim 1, wherein the dsRNA is expressed in a bacterial or yeast cell.

6. The dsRNA of claim 1, further comprising a T7 RNA polymerase promoter sequence.

7. A double-stranded ribonucleic acid (dsRNA) comprising a sense region comprising a sequence with at least 99% or 100% sequence identity to at least 21 consecutive nucleotides of SEQ ID NO: 2, and an antisense region comprising a second sequence complementary to the sense region.

8. The dsRNA of claim 7, wherein the dsRNA is expressed in a plant cell.

9. The dsRNA of claim 8, wherein the plant cell is a hardwood tree cell.

10. The dsRNA of claim 7, wherein the dsRNA is expressed in a bacterial or yeast cell.

11. A DNA molecule comprising a promoter functional in a host cell and a DNA encoding a dsRNA comprising a first region and a second region, wherein the first region comprises a sense region with at least 99% or 100% sequence identity to SEQ ID NO: 2, and a second region complementary to the first region.

12. The DNA molecule of claim 11, wherein the host cell is a bacterial cell, a yeast cell or a plant cell.

13. A host cell comprising the DNA molecule of claim 11 or 12.

14. The host cell of claim 13, wherein the host cell is a hardwood tree cell.

15. A transgenic plant cell, transgenic plant or transgenic seed comprising a dsRNA of claim 1 or claim 7.

16. The plant cell, plant or seed of claim 15, wherein the plant cell, plant or seed is a hardwood tree cell, hardwood tree, or hardwood tree seed.

17. A method of controlling *L. dispar* comprising applying the dsRNA of claim 1 or 7 to a plant on which one or more *L. dispar* insects feed and allowing the one or more insects to ingest an effective amount of the dsRNA, thereby controlling the one or more *L. Dispar* insects.

18. The method of claim 17, wherein the dsRNA is present in a transgenic bacterial cell.

19. The method of claim 17, wherein the the dsRNA comprises a first dsRNA molecule and a second dsRNA molecule, wherein the first dsRNA molecule comprises a sense region with at least 99% or 100% sequence identity to SEQ ID NO: 2 and an antisense region comprising a second sequence complementary to the sense region and wherein the second dsRNA molecule comprises a sense region with at least 99% or 100% sequence identity to SEQ ID NO: 3 and an antisense region comprising a second sequence complementary to the sense region.

20. A method of controlling *L. dispar* comprising, planting or growing a transgenic plant expressing the dsRNA of claim 1 or claim 7 and allowing one or more insects to ingest an effective amount of the dsRNA, thereby controlling the one or more insects.

21. The method of claim 20, wherein the dsRNA comprises a first dsRNA molecule and a second dsRNA molecule, wherein the first dsRNA molecule comprises a sense region with at least 99% or 100% sequence identity to SEQ ID NO: 2 and an antisense region comprising a second sequence complementary to the sense region and wherein the second dsRNA molecule comprises a sense region with at least 99% or 100% sequence identity to SEQ ID NO: 3 and an antisense region comprising a second sequence complementary to the sense region.

* * * * *

SEQUENCE LISTING

<160> NUMBER OF SEQ ID NOS: 43

<210> SEQ ID NO 1
<211> LENGTH: 500
<212> TYPE: DNA
<213> ORGANISM: Lymantria dispar

<400> SEQUENCE: 1

```
atgcatatgc gtgcaaggtt tccttaatca gccggcagcc acgacaagtc ccgtaaccac        60
cagaaacaca atatttgctg atgaaaaatt tgaaggtgaa atcttcgaag atctcgatgt       120
atttgaacaa ttagacataa ctgcaagaaa cagtgaactc tacagattac cgaacaccac       180
aaaaccgagt cactataccg tcttgtggac gctggacttc tcacgagcaa ttccaacaca       240
atctggcacg gtttcaatat tgctaaatgc tactcaggct aatgttaatg aaatagtaat       300
ccacgctcac aatctaacca ttaccaatgt aagactacag ttaggtacta cagaagtccc       360
agtcacctat actttagaac cagaatatca tttcatgaga attcgattaa acgaaggttc       420
gttgaactat aatcccacaa ctcctcaata ctatactctc acaatcgatt ttggtgccaa       480
tctgcgtgat gacatgtacg                                                   500
```

<210> SEQ ID NO 2
<211> LENGTH: 208
<212> TYPE: DNA
<213> ORGANISM: Lymantria dispar

<400> SEQUENCE: 2

```
tttttggaag taaaaccacg atttaaacaa cagaggtaca ggatggatga aattattgaa        60
atagaactat atgtgagatt gtcatacaac acagttcttg aagtaaagaa atgctctgta       120
gctatatctg gtcacactga aactattgaa atatcaataa ctgataatga caatactgtt       180
atatctttgg aaggtggtag agttaaga                                          208
```

<210> SEQ ID NO 3
<211> LENGTH: 250
<212> TYPE: DNA
<213> ORGANISM: Lymantria dispar

<400> SEQUENCE: 3

```
tttacataaa tacagccaca ttggttggac catattttct accatatcaa taaagcttat     60
acaaaaatct aagtttatac aaaatcattt tctactaatt tacaaggaca catatgaaac    120
tactacgctg gtagcaattt cagacatgtg gtcacactga aaaagctgca agctttaaaa    180
ggatcaccat tagctttaaa caacgttatg tcatatttta ataaaatgcg attcttaatg    240
caaatctgct                                                           250

<210> SEQ ID NO 4
<211> LENGTH: 500
<212> TYPE: DNA
<213> ORGANISM: Lymantria dispar

<400> SEQUENCE: 4
tggatctgca agatcagctc gtagctatga acctttagcc aatgatcctc agacgagaga     60
acttcagatt aacgaaagaa tagctgataa cgttggcgac ttcttagaca atcacgtact    120
gcaattgcgt ctaaccgaac ctgatggtga atcccgatct cttgatgagg aagctcgtgg    180
caagaagatc aagaagaaga agctcaagaa gctgttgccc ctccttctcc ttttgaagct    240
gaaattcgct gccctcattc cacttttcct tggtatcatc gcaatcgttg ccgttaaagc    300
cgtcttcctt ggaaagattg cattcgccat gaatgcaatc agcttgataa gaaaacttat    360
ggcaaagaag aatggaggag gttcctcatc gagcatttcc tgggctgctc ctcaacatac    420
ggatgagcat ccaggatatt cttatgaacc cgctcagtct caaggatggg gtcggcaggc    480
cagtgatggc gcggacttag                                                500

<210> SEQ ID NO 5
<211> LENGTH: 500
<212> TYPE: DNA
<213> ORGANISM: Lymantria dispar

<400> SEQUENCE: 5
cacgccttgg aatcgtataa actattctag aagtagccag tataagtggt agcaacattc     60
tcctgaaatg tttgtatcaa taactgcgat aaccaactag ctgctcaagc ttaaccctgg    120
atagtctatt taactgaaag tctactctga aggctgacgc tctagttata tctcacagac    180
gacgagtgtc gttgatgtta ggtgcgctaa tttatactaa gcaccgacat cgctccaaat    240
atcccttcag tagttctgcg tgacgatcct agacgttatg gtagtgacgt cattgttttc    300
tctcacggca cactcacaac gaccctatac acaaacgcat actgattaga catgctgtgc    360
atttgaagtt tcagatctgg atactagaat aacattacac cggtttcgta tactatagtg    420
aatacgaaat tatttcagaa tatccgagtt tcgaattatc caacagtttc ggattatcct    480
acgattacgg gttatccgac                                                500

<210> SEQ ID NO 6
<211> LENGTH: 223
<212> TYPE: DNA
<213> ORGANISM: Artificial Sequence
<220> FEATURE:
<223> OTHER INFORMATION: Chemically Synthesized

<400> SEQUENCE: 6
taatacgact cactataggg agaccggcag atctgatatc atcgatgaat tcgagctcca     60
ccgcggtggc ggccgctcta gaactagtgg atccaccggt tccatggcta gccacgtgac    120
gcgtggatcc cccgggctgc aggaattcga tatcaagctt atcgataccg tcgacctcga    180
```
gggggggccc ggtacccaat tcgccctata gtgagtcgta tta         223

<210> SEQ ID NO 7
<211> LENGTH: 595
<212> TYPE: DNA
<213> ORGANISM: Escherichia coli

<400> SEQUENCE: 7
tgaaagctgg ctacaggaag gccagacgcg aattattttt gatggcgtta actcggcgtt    60
tcatctgtgg tgcaacgggc gctgggtcgg ttacggccag acagtcgtt tgccgtctga    120
atttgacctg agcgcatttt tacgcgccgg agaaaaccgc ctcgcggtga tggtgctgcg   180
ctggagtgac ggcagttatc tggaagatca ggatatgtgg cggatgagcg gcattttccg   240
tgacgtctcg ttgctgcata aaccgactac acaaatcagc gatttccatg ttgccactcg   300
ctttaatgat gatttcagcc gcgctgtact ggaggctgaa gttcagatgt gcggcgagtt   360
gcgtgactac ctacgggtaa cagtttcttt atggcagggt gaaacgcagg tcgccagcgg   420
caccgcgcct ttcggcggtg aaattatcga tgagcgtggg ggttatgccg atcgcgtcac   480
actacgtctg aacgtcgaaa acccgaaact gtggagcgcc gaaatcccga atctctatcg   540
tgcggtggtt gaactgcaca ccgccgacgg cacgctgatt gaagcagaag cctgc        595

<210> SEQ ID NO 8
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 8
atgcatatgc gtgcaaggt                                                19

<210> SEQ ID NO 9
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 9
cgtacatgtc atcacgcaga                                               20

<210> SEQ ID NO 10
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 10
tttttggaag taaaaccacg a                                             21

<210> SEQ ID NO 11
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 11
tcttaactct accaccttcc aaaga                                         25

<210> SEQ ID NO 12
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 12
tttacataaa tacagccaca ttggt                                   25

<210> SEQ ID NO 13
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 13
agcagatttg cattaagaat cg                                      22

<210> SEQ ID NO 14
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 14
tggatctgca agatcagctc                                         20

<210> SEQ ID NO 15
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 15
ctaagtccgc gccatcact                                          19

<210> SEQ ID NO 16
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 16
cacgccttgg aatcgtataa a                                       21

<210> SEQ ID NO 17
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 17
gtcggataac ccgtaatcgt                                         20

<210> SEQ ID NO 18
<211> LENGTH: 46
<212> TYPE: DNA
<213> ORGANISM: Artificial Sequence
<220> FEATURE:
<223> OTHER INFORMATION: Chemically Synthesized

<400> SEQUENCE: 18
gaattaatac gactcactat agggagaatg catatgcgtg caaggt    46

<210> SEQ ID NO 19
<211> LENGTH: 47
<212> TYPE: DNA
<213> ORGANISM: Artificial Sequence
<220> FEATURE:
<223> OTHER INFORMATION: Chemically Synthesized

<400> SEQUENCE: 19
gaattaatac gactcactat agggagacgt acatgtcatc acgcaga    47

<210> SEQ ID NO 20
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 20
gaattaatac gactcactat agggagattt ttggaagtaa aaccacga    48

<210> SEQ ID NO 21
<211> LENGTH: 52
<212> TYPE: DNA
<213> ORGANISM: Artificial Sequence
<220> FEATURE:
<223> OTHER INFORMATION: Chemically Synthesized

<400> SEQUENCE: 21
gaattaatac gactcactat agggagatct taactctacc accttccaaa ga    52

<210> SEQ ID NO 22
<211> LENGTH: 52
<212> TYPE: DNA
<213> ORGANISM: Artificial Sequence
<220> FEATURE:
<223> OTHER INFORMATION: Chemically Synthesized

<400> SEQUENCE: 22
gaattaatac gactcactat agggagattt acataaatac agccacattg gt    52

<210> SEQ ID NO 23
<211> LENGTH: 49
<212> TYPE: DNA
<213> ORGANISM: Artificial Sequence
<220> FEATURE:
<223> OTHER INFORMATION: Chemically Synthesized

<400> SEQUENCE: 23
gaattaatac gactcactat agggagaagc agatttgcat taagaatcg    49

<210> SEQ ID NO 24
<211> LENGTH: 47
<212> TYPE: DNA
<213> ORGANISM: Artificial Sequence
<220> FEATURE:
<223> OTHER INFORMATION: Chemically Synthesized

<400> SEQUENCE: 24
gaattaatac gactcactat agggagatgg atctgcaaga tcagctc    47

<210> SEQ ID NO 25
<211> LENGTH: 46

<212> TYPE: DNA
<213> ORGANISM: Artificial Sequence
<220> FEATURE:
<223> OTHER INFORMATION: Chemically Synthesized

<400> SEQUENCE: 25
gaattaatac gactcactat agggagacta agtccgcgcc atcact            46

<210> SEQ ID NO 26
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 26
gaattaatac gactcactat agggagacac gccttggaat cgtataaa          48

<210> SEQ ID NO 27
<211> LENGTH: 47
<212> TYPE: DNA
<213> ORGANISM: Artificial Sequence
<220> FEATURE:
<223> OTHER INFORMATION: Chemically Synthesized

<400> SEQUENCE: 27
gaattaatac gactcactat agggagagtc ggataacccg taatcgt           47

<210> SEQ ID NO 28
<211> LENGTH: 45
<212> TYPE: DNA
<213> ORGANISM: Artificial Sequence
<220> FEATURE:
<223> OTHER INFORMATION: Chemically Synthesized

<400> SEQUENCE: 28
gaattaatac gactcactat agggagatga aagctggcta cagga             45

<210> SEQ ID NO 29
<211> LENGTH: 45
<212> TYPE: DNA
<213> ORGANISM: Artificial Sequence
<220> FEATURE:
<223> OTHER INFORMATION: Chemically Synthesized

<400> SEQUENCE: 29
gaattaatac gactcactat agggagagca ggcttctgct tcaat             45

<210> SEQ ID NO 30
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 30
caactcctca atactatact ctcacaatcg                              30

<210> SEQ ID NO 31
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 31
tcagtaggat tgttcctgaa ccaa                                          24

<210> SEQ ID NO 32
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 32
ctctgtagct atatctggtc acactgaa                                      28

<210> SEQ ID NO 33
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 33
tctcttaact ctaccacctt ccaaaga                                       27

<210> SEQ ID NO 34
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 34
agccacattg gttggaccat                                               20

<210> SEQ ID NO 35
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 35
gcgtagtagt ttcatatgtg tccttgta                                      28

<210> SEQ ID NO 36
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 36
tcctgaagga cttggatatc tttga                                         25

<210> SEQ ID NO 37
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 37
gtctgaggat cattggctaa aggt                                          24

<210> SEQ ID NO 38
<211> LENGTH: 24
<212> TYPE: DNA
<213> ORGANISM: Artificial Sequence

```
<220> FEATURE:
<223> OTHER INFORMATION: Chemically Synthesized

<400> SEQUENCE: 38
cgaaaaaatc caccattact ttca                                          24

<210> SEQ ID NO 39
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 39
ttcaggagaa tgttgctacc actt                                          24

<210> SEQ ID NO 40
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 40
gtctcgcagc cgtattaagg cga                                           23

<210> SEQ ID NO 41
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 41
gcactcatcc catcactggt caga                                          24

<210> SEQ ID NO 42
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 42
ccggtaacga acgagactct a                                             21

<210> SEQ ID NO 43
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 43
gggcatcaca gacctgttat t                                             21
```